US007565250B2

(12) United States Patent
Shain et al.

(10) Patent No.: US 7,565,250 B2
(45) Date of Patent: Jul. 21, 2009

(54) METHOD AND SYSTEM FOR ANALYZING REACTIONS USING AN INFORMATION SYSTEM

(75) Inventors: Eric B. Shain, Glencoe, IL (US); John M. Clemens, Wadsworth, IL (US); Tzyy-Wen Jeng, Vernon Hills, IL (US); George J. Schneider, Barrington, IL (US)

(73) Assignee: Abbott Laboratories Inc., Abbott Park, IL (US)

(*) Notice: Subject to any disclaimer, the term of this patent is extended or adjusted under 35 U.S.C. 154(b) by 668 days.

(21) Appl. No.: 10/991,025

(22) Filed: Nov. 17, 2004

(65) Prior Publication Data

US 2005/0130211 A1    Jun. 16, 2005

Related U.S. Application Data

(60) Provisional application No. 60/527,389, filed on Dec. 6, 2003.

(51) Int. Cl.
*G06F 19/00* (2006.01)
*C12P 19/34* (2006.01)
*C12Q 1/68* (2006.01)

(52) U.S. Cl. .............................. 702/19; 702/127; 435/6; 435/91.2

(58) Field of Classification Search ........................ None
See application file for complete search history.

(56) References Cited

U.S. PATENT DOCUMENTS

| | | | |
|---|---|---|---|
| 5,270,184 A | 12/1993 | Walker et al. | |
| 5,538,848 A | 7/1996 | Livak et al. | |
| 5,723,591 A | 3/1998 | Livak et al. | |
| 5,876,930 A | 3/1999 | Livak et al. | |
| 6,303,305 B1 | 10/2001 | Wittwer et al. | |
| 7,228,237 B2 * | 6/2007 | Woo et al. ..................... 702/19 | |

FOREIGN PATENT DOCUMENTS

| | | |
|---|---|---|
| EP | 0 320 308 B1 | 11/1993 |
| EP | 0 686 699 | 12/1995 |
| EP | 1 041 158 | 10/2000 |
| EP | 1 138 783 | 10/2001 |
| EP | 1 138 784 | 10/2001 |

OTHER PUBLICATIONS

Livak, et al., Analysis of Relative Gene Expression Data Using Real-Time Quantitative PCR and the $2^{-\Delta\Delta C_T}$ Method, Methods 25, 402-408 (2001).
Bustin, Absolute quantification of mRNA using real-time reverse transcription PCR assays, *Journal of Molecular Endocrinology* (2000) 25, 169-193.
Bustin, Quantification of mRNA using real-time reverse transcription PCR (RT-PCR): trends and problems, *Journal of Molecular Endocrinology* (2002) 29, 23-39.
Myers, et al., Reverse Transcription and DNA Amplification by a *Thermus thermophilus* DNA Polymerase, *Biochemistry*, vol. 30, No. 31, 1991, 7661-7666.
Kievits, et al., NASBA™ isothermal enzymatic in vitro nucleic acid amplification optimized for the diagnosis of HIV-1 infection, *Journal of Virological Methods*, 35 (1991) 273-286.
Kwoh, et al., Transcription-based amplification system and detection of amplified human immunodeficiency virus type 1 with a bead-based sandwich hybridization format, *Proc. Natl. Acad. Sci. USA*, vol. 86, pp. 1173-1177 (1989).
Landegren, et al., A Ligase-Mediated Gene Detection Technique, *Science*, vol. 241, 1077-1080 (1988).
Saiki, et al., Enzymatic Amplification of β-Globin Genomic Sequences and Restriction Site Analysis for Diagnosis of Sickle Cell Anemia, *Science*, vol. 230, 1350-1354 (1985).
Hatch, et al., Rolling circle amplification of DNA immobilized on solid surfaces and its application to multiplex mutation detection, *Genetic Analysis: Biomolecular Engineering* 15 (1999) 35-40.
Saiki, et al., Primer-Directed Enzymatic Amplification of DNA with a Thermostable DNA Polymerase, *Science*, vol. 239, 487-491 (1988).
Wu, et al., The Ligation Amplification Reaction (LAR)—Amplification of Specific DNA Sequences Using Sequential Rounds of Template-Dependent Ligation, *Genomics* 4, 560-569 (1989).
Lisby, Application of Nucleic Acid Amplification in Clinical Microbiology, *Molecular Biotechnology*, vol. 12, 75-99 (1999).
Walker, et al., Isothermal in vitro amplification of DNA by a restriction enzyme/DNA polymerase system, *Proc. Natl. Acad. Sci. USA*, vol. 89, pp. 392-396 (1992).

* cited by examiner

*Primary Examiner*—Lori A. Clow
(74) *Attorney, Agent, or Firm*—David L. Weinstein

(57) ABSTRACT

A method and system for determining the quantity of an analyte initially present in a chemical and or biological reaction as well as a computer implemented method and system to automate portions of the analysis comprising mathematical or graphical analysis of an amplification reaction.

12 Claims, 22 Drawing Sheets

| Log(Sample) | Mean Log Concentrations | | | |
|---|---|---|---|---|
| | Conc(FCN) | Conc(FCN2) | Conc(FCN$_{MR\ Adj.}$) | Conc(FCN$_{Int.\ Adj.}$) |
| 1.7 | 2.14 | 1.58 | 1.73 | 1.63 |
| 2.7 | 2.70 | 2.63 | 2.68 | 2.63 |
| 3.7 | 3.58 | 3.69 | 3.65 | 3.69 |
| 4.7 | 4.57 | 4.75 | 4.62 | 4.70 |
| 5.7 | 5.63 | 5.66 | 5.65 | 5.65 |
| 6.7 | 6.76 | 6.71 | 6.73 | 6.69 |

FIG. 16 QUANTIFICATION RESULTS

| | Mean Log Concentrations | | | |
|---|---|---|---|---|
| Log(Sample) | Conc(FCN) | Conc(FCN2) | Conc(FCN$_{MR\ Adj.}$) | Conc(FCN$_{Int.\ Adj.}$) |
| 1.7 | 2.43 | 1.77 | 1.88 | 1.64 |
| 2.7 | 2.95 | 2.73 | 2.80 | 2.63 |
| 3.7 | 3.76 | 3.71 | 3.74 | 3.68 |
| 4.7 | 4.68 | 4.69 | 4.68 | 4.67 |
| 5.7 | 5.65 | 5.53 | 5.69 | 5.61 |
| 6.7 | 6.70 | 6.49 | 6.74 | 6.64 |

FIG. 17 RESULTS OF ONE POINT CALIBRATION

Polynomial Fit Degree=3

METHOD AND SYSTEM FOR ANALYZING REACTIONS USING AN INFORMATION SYSTEM

RELATED APPLICATIONS

The present application claims priority from of U.S. Provisional Patent Application No. 60/527,389, filed Dec. 6, 2003.

COPYRIGHT NOTICE

Pursuant to 37 C.F.R. 1.71(e), applicants note that this disclosure contains material that is subject to and for which is claimed copyright protection, such as, but not limited to, source code listings, screen shots, user interfaces, user instructions, and any other aspects of this submission for which copyright protection is or may be available in any jurisdiction. The copyright owner has no objection to the facsimile reproduction by anyone of the patent document or patent disclosure, as it appears in the records of the Patent and Trademark Office. All other rights are reserved, and all other reproduction, distribution, creation of derivative works based on the contents, public display, and public performance of the application or any part thereof are prohibited by applicable copyright law.

BACKGROUND OF THE INVENTION

1. Field of the Invention

The present invention relates to analysis of data of nucleic acid amplification reactions. More specifically, the invention relates to an information system and method for making determinations regarding chemical and/or biological reactions. The invention also involves an alternate method of quantifying nucleic acids in a sample comprising amplification of a target nucleic acid and analysis of data obtained during the amplification reaction. The invention further involves a diagnostic system and/or kit using real-time nucleic acid amplification including, but not limited to, PCR analysis.

2. Discussion of the Art

In many different industrial, medical, biological, and/or research fields, it is desirable to determine the quantity of a nucleic acid of interest. Some methods of quantifying nucleic acids of interest involve amplifying them and observing a signal proportional to the quantity of amplified products made; other methods involve generating a signal in response to the presence of a target nucleic acid, which signal accumulates over the duration of the amplification reaction. As used herein, nucleic acid amplification reaction refers both to amplification of a portion of the sequence of a target nucleic acid and to amplification and accumulation of a signal indicative of the presence of a target nucleic acid, with the former often being preferred to the latter. The quantification of nucleic acids is made more difficult or less accurate or both because data captured during amplification reactions are often significantly obscured by signals that are not generated in response to the target nucleic acid (i.e., noise). Furthermore, the data captured by many monitoring methods can be subject to variations and lack of reproducibility due to conditions that can change during a reaction or change between different instances of a reaction. In view of the above, there is a need to develop improved means of quantifying a nucleic acid. Where quantification of nucleic acids is enabled by amplification reactions, there is also a need to improve current methods of detecting suspect or invalid amplification reactions. There further remains a need to improve current abilities to distinguish between amplification reactions that do not detect a target nucleic acid (i.e., negative reactions) from weak signals obtained from amplification reactions suffering from low quantities of a target nucleic acid in a sample, a degree of inhibition of the amplification reaction, or other causes. The present invention provides improvements in these areas as is disclosed below.

A non-exhaustive list of references providing background information regarding the present invention follows:

Livak, K. and Schmittgen, T., *Analysis of Relative Gene Expression Data Using Real-Time Quantitative PCR and the 22DDCT Method, METHODS* 25: 402-408 (2001) doi: 10.1006/meth.2001.1262.

Bustin S A, *Absolute quantification of mRNA using real-time reverse transcription PCR assays, Journal of Molecular Endocrinology* 25: 169-193 (2000).

Bustin S A., *Quantification of mRNA using real-time reverse transcription PCR: trends and problems, J Mol Endocrinol.* 29: 23-29 (2002).

While the inventors cannot guarantee that the following website will remain available and do not necessarily endorse any opinions expressed therein, an interested person may wish to refer to the world wide web at wzw.tum.de/gene-quantification/index.shtml for useful background information.

The discussion of any works, publications, sales, or activity anywhere in this submission, including in any documents submitted with this application, is not intended to be an admission of any manner that any such work constitutes prior art, unless explicitly stated to the contrary. Similarly, the discussion of any activity, work, or publication herein is not an admission that such activity, work, or publication was known in any particular jurisdiction.

Real-time PCR is an amplification reaction used for the quantification of target nucleic acids in a test sample. Conventionally, skilled artisans typically view the amplification reaction as comprising three distinct phases. First, there is a background or baseline phase, in which the target nucleic acid is being amplified but the signal proportional to the quantity of the target nucleic acid cannot be detected because it is too small to be observed relative to signals independent of the target (sometimes called "background" or "background signal"). Next, there is a logarithmic phase in which the signal grows substantially logarithmically because the signal is substantially proportional to the quantity of target nucleic acid in the amplification reaction and is greater than the background signal. Finally, the growth in the signal slows during a "plateau" phase reflecting less than logarithmic amplification of the target nucleic acid. As is known in the art, the time at which the logarithmic phase crosses a threshold value, which is a value somewhat greater than the value of the background signal, is reproducibly related to the log of the concentration of the target nucleic acid. This prior art method is generically referred to as the $C_t$ method, perhaps so named for the Cycle at which the signal crosses the threshold. $C_t$ analysis is reasonably reproducible and accurate, but suffers from some drawbacks, which need not be discussed here to understand the present invention.

U.S. Pat. No. 6,303,305 discloses a method of quantification of nucleic acids employing PCR reactions. The method disclosed employs the nth derivative of the growth curve of a fluorescent nucleic acid amplification reaction. This method effectively avoids the need to perform a baseline correction, but provides no reliable method of determining reactive from non-reactive samples, and does not reasonably suggest how to use an nth derivative calculation to assess the validity of the results obtained. In addition, nucleic acid amplification signals resulting from any artifacts in the system (e.g., crosstalk or positive bleedover—defined infra) cannot be distinguished from true positive responses using the methods disclosed therein and can lead to false positive results. However, the first derivative calculation disclosed by U.S. Pat. No. 6,303,305 provides an efficiency related value that is useful in the context of the present invention. The skilled artisan can refer to U.S. Pat. No. 6,303,305 for additional details relating to calculation of a first derivative of a nucleic acid amplification signal growth curve. U.S. Pat. No. 6,303,305 is incorporated by reference only in the United States of America, and other jurisdictions permitting incorporation by reference, to the extent it discloses the calculation of the first derivative of a nucleic acid amplification growth curve. However, U.S. Pat. No. 6,303,305 does not disclose or suggest the uses of this efficiency related value described in this disclosure (below).

Co-owned U.S. Provisional Patent Application No. 60/527,389, filed Dec. 6, 2003, discloses a method for analyzing a nucleic acid amplification reaction in which the log of the signal from an amplification reaction is examined for the maximum gradient or slope. This value, which for any data set corresponds to a point a certain period of time or number of cycles after the initiation of the amplification reaction, is called the MGL of the reaction. The MGL is useful in certain embodiments of the present invention, particularly in those that distinguish qualitatively those samples comprising little target nucleic acid from those samples that do not contain target nucleic acid. U.S. Patent Application No. 60/527,389, filed Dec. 6, 2003 is incorporated herein by reference in its entirety.

SUMMARY OF THE INVENTION

The present invention provides a method for determining whether a sample contains a nucleic acid of interest, for quantifying this nucleic acid, and for assessing the validity or quality of the data used to reach the preceding qualitative and quantitative determinations.

The method of this invention method comprises contacting a sample with amplification or detection reagents or both in order to amplify the nucleic acid (as the term "amplified" is used herein). The amplification reaction generates signals indicative of the quantity of the target nucleic acid present in the sample, which signals are recorded at numerous points during the amplification reaction. The signal can be measured and recorded as a function of time value, or in the alternative, cycle number.

Suitable "efficiency related transforms" viewed or calculated as a function of time are determined for the amplification reaction, and the point in the amplification reaction of the maximum of the efficiency related transform, the magnitude of the maximum of the efficiency related transform, or the width (or similar parameter) of a peak in the plot of the efficiency related transform as a function of time can be used to obtain information about the reaction. This point in the reaction represents the point in time or the amplification cycle at which the maximum of the efficiency related transform occurs. Advantageously, the maximum of the efficiency related transform for a particular reaction, as well as the duration and magnitude of substantial changes in the calculated efficiency related transform, have consistently reproducible relationships to the initial concentration of a target nucleic acid in a sample, to the reliability of the data and information generated by the assay, to the presence or absence of a bona fide target nucleic acid, and to other parameters of the reaction. Advantageously, these relationships hold even in the presence of substantial noise and unpredictable variations in the signal(s) generated by the amplification reaction. As used herein, the term "maximum", as applied to efficiency related transforms, is intended to include the minimum of the efficiency related transform when the reciprocal of the efficiency related transform is used. One can use the inverse ratio, in which, in the case of a curve, the curve will start at a value of approximately 1 in the baseline region, decrease during the growth region, and return approximately to one in the plateau region. The use of this transform would allow one to use the magnitude and the position of the trough instead of the magnitude and position of the peak for analysis. This transform is implemented in a manner that essentially equivalent to the ratio method in which the maximum of the efficiency related transform for a particular reaction is employed.

In all embodiments, signals from the amplification reaction are measured at intervals of time appropriate for the amplification reaction during the amplification reaction. These signals can be referred to as time-based or periodic measurements, such that every measurement of the signal generated for a particular reaction can be expressed as a function of time. In some embodiments, the amplification reaction is cyclical (e.g., as in PCR). Because cycles often have a substantially uniform duration, it is frequently convenient to substitute a "cycle number" for a time measurement. Accordingly, in some embodiments of the present invention, a region of data identified by one or more methods on an information processing system as described herein can correspond to a cycle number. However, some cyclical amplification reactions have cycles of non-uniform duration. For these amplification reactions, it may be preferable to measure time in non-uniform measures. For example, the theoretical extent of amplification in a PCR reaction having cycles of varying duration will be linked more directly to the number of cycles performed rather than the duration of the reaction. Accordingly, the skilled artisan will readily appreciate that the time-based measurements can easily be scaled to reflect the underlying amplification reaction. As is known in the art, it is often useful to interpolate data and results between cycle numbers, which gives rise to the concept of a fractional cycle number "FCN." Similarly, in reactions where measurements are based on time, events can be measured in fractional time units.

In further embodiments, the invention advantageously involves a system or method or both for analyzing a reaction sample, such as a PCR reaction sample, that uses a substantial set of available reaction kinetics data to identify a region of interest, rather than using a very limited data set, such as where a reaction curve crosses a threshold.

In certain embodiments, an identified region can be used to determine one or more qualitative results, or quantitative data analysis results, or both. The reaction point of the maximum of the efficiency related transform can be used to determine the concentration of a target nucleic acid in a sample or to determine qualitatively whether any target analyte is present in a test sample. These and other values can be compared with reference quantities in generally the same way that a threshold cycle number ($C_t$) or fractional threshold cycle number can be used in the prior art.

The reaction point corresponding to the maximum of the efficiency related transform can be understood as indicating or being derived from a cycle number that is located at a relatively consistent point with respect to reaction efficiency, such as at a maximum of reaction efficiency or a region consistently related to a maximum of reaction efficiency or consistently related to some other reaction progression. Different methods can be used to determine a reaction point related to a maximum of reaction efficiency. This value can comprise adjusted FCN values (e.g., $FCN_{MR\ Adj.}$ and $FCN_{Int.\ Adj.}$), as described below. In certain embodiments of this invention, methods of the invention can determine FCN values for multiple reaction signals, such as a target and/or a control and use those values in determining reaction parameters, including, but not limited to, quantity of target nucleic acid initially present in a sample and the validity of the results generated by an amplification reaction.

The present invention can identify a value indicative of the reaction efficiency (at times, herein, generally referred to as an "efficiency related value" (ERV)) at one or more regions on a signal growth curve. A specific efficiency related value is referred to as a MaxRatio value or MR. MaxRatio refers to one possible method for calculating an efficiency related value as further discussed herein. This is one example of a method for determining an ERV and illustrative examples herein that refer to MR should also be understood to include other suitable methods for determining an efficiency related value, including, but not limited to, the maximum gradient of the log of the growth curve, as described in co-owned U.S. patent application Ser. No. 60/527,389, filed Dec. 6, 2003, the maximum first derivative of the signal obtained from the amplification reaction (e.g., as disclosed in U.S. Pat. No. 6,303,305), and the maximum difference between two sequential signals obtained from the amplification reaction. Thus, this invention is involved with an analytical method that identifies two values for a reaction curve: (1) one value related to a cycle number or time value and (2) one value indicating an efficiency related value. The invention can use those two values in analysis of reaction data performed using an information-handling system and method of using the system. An example of two such values are FCN and MR specific embodiments discussed below.

This invention is also involved with a method and system that uses two values as discussed above that are determined from a reaction under examination to compare that reaction to one or more criteria data sets. A criteria comparison can be used to determine and/or correct any results and/or quantifications as described herein. Criteria data can be derived by generating pairs of cycle number related values-efficiency related values (e.g., FCN-MR pairs) from multiple calibration reactions of known quantity or known concentration or both.

This invention also involves one or more techniques for performing efficiency analysis of reaction data. This analysis can be used separately from or in conjunction with the cycle number related value-efficiency related value analysis discussed herein. Efficiency analysis can be used to find a region of interest for making a determination about reaction data, such as, for comparison to calibration data sets, in a way similar to $C_t$ analysis as understood in the art.

The present invention also provides a method for analyzing a nucleic acid amplification reaction, in which a sample containing a nucleic acid is contacted with amplification agents and placed under suitable amplification conditions to amplify a portion of the nucleic acid in the sample. During the amplification reaction, signals that are proportional to the amount of the target nucleic acid present are periodically measured at a suitable interval. Conveniently, the interval can correspond to the duration of a cycle for those amplification reactions that are cyclical. The signals are then manipulated to determine an efficiency related transform for the amplification reaction. Any suitable efficiency related transform can be used for the invention. Efficiency related transforms preferred in the context of the present invention include the slope of the line, which can be determined by many techniques, including, but not limited to, difference calculations on sequential data points, determining the first derivative of a line fitted to the growth curve of the reaction signal, and determining the gradient, slope, or derivative of the log of the growth curve (i.e., Log (growth curve)). More preferably, the efficiency related transform is the ratio of sequential data points, sometimes referred to herein as the ratio curve. When the efficiency related transform for the reaction is known, a plot of the efficiency related transform as a function of time (preferably expressed in the units used to measure the signal) (or mathematical manipulation yielding information similar to a plot) can be used to identify a peak value. However, a plot is not required. The width of the peak in the selected range of acceptable peak widths can be determined by any suitable technique or method. However, a preferred method for determining the acceptable peak width involves statistically analyzing the degree of variance in peak widths obtained from objectively normal amplification reactions that are very similar to or even identical to the amplification method analyzed by the method of this invention. In the reaction analyzed, an unknown test sample is usually used in place of samples used to characterize the amplification reaction or an analyte assay. If the peak width of the analyzed amplification reaction falls within the prescribed range of acceptable peak widths, the reaction is declared normal; if the peak width of the analyzed amplification reaction does not fall within the prescribed range of acceptable peak widths, the reaction is identified as having provided sub-optimal, aberrant, or otherwise questionable signals. The width of the leading half of the efficiency related transform peak is evaluated. This evaluation is a more forgiving measurement of amplification reaction validity, and therefore may be preferred in some instances, but generally not in all instances.

The invention further involves an information system and/or program able to analyze captured data. Data can be captured as image data from observable features of the data, and the information system can be integrated with other components for capturing, preparing, and/or displaying sample data. Representative examples of systems in which the invention can be employed include, but are not limited to, the BioRad® i-Cycler®, the Stratagene® MX4000®, and the ABI Prism 7000® systems. Similarly, the present invention provides a computer product capable of executing the method of this invention.

Various embodiments of the present invention provide methods and/or systems that can be implemented on a general purpose or special purpose information handling system by means of a suitable programming language, such as Java, C++, C#, Cobol, C, Pascal, Fortran, PL1, LISP, assembly, etc., and any suitable data or formatting specifications, such as HTML, XML, dHTML, TIFF, JPEG, tab-delimited text, binary, etc. For ease of discussion, various computer software commands useful in the context of the present invention are illustrated in MATLAB® commands. The MATLAB software is a linear algebra manipulator and viewer package commercially available from The Mathworks, Natick, Mass. (USA). Of course, in any particular implementation (as in any software development project), numerous implementation-specific decisions can be made to achieve the developer's specific goals, such as compliance with system-related and/or business-related constraints, which will vary from one implementation to another. Moreover, it will be appreciated that such a developmental effort might be complex and time-consuming, but would nevertheless be a routine undertaking of software engineering for those of ordinary skill in the art having the benefit of this disclosure.

The invention will be better understood with reference to the following drawings and detailed descriptions. For purposes of clarity, this discussion refers to devices, methods, and concepts in terms of specific examples. However, the invention and aspects thereof may have applications to a variety of types of devices and systems.

Furthermore, it is well known that logic systems and methods such as those described herein can include a variety of different components and different functions in a modular fashion. Different embodiments of the invention can include different combinations of elements and functions and may group various functions as parts of various elements. For purposes of clarity, the invention is described in terms of systems that include many different components and combinations of novel components and known components. No inference should be taken to limit the invention to combinations requiring all of the novel components in any illustrative embodiment of this invention.

As used herein, "the invention" should be understood to include one or more specific embodiments of the invention (unless explicitly indicated to the contrary). Many variations according to the invention will be understood from the teachings herein to those of ordinary skill in the art.

DETAILED DESCRIPTION OF THE INVENTION

Figure 1:
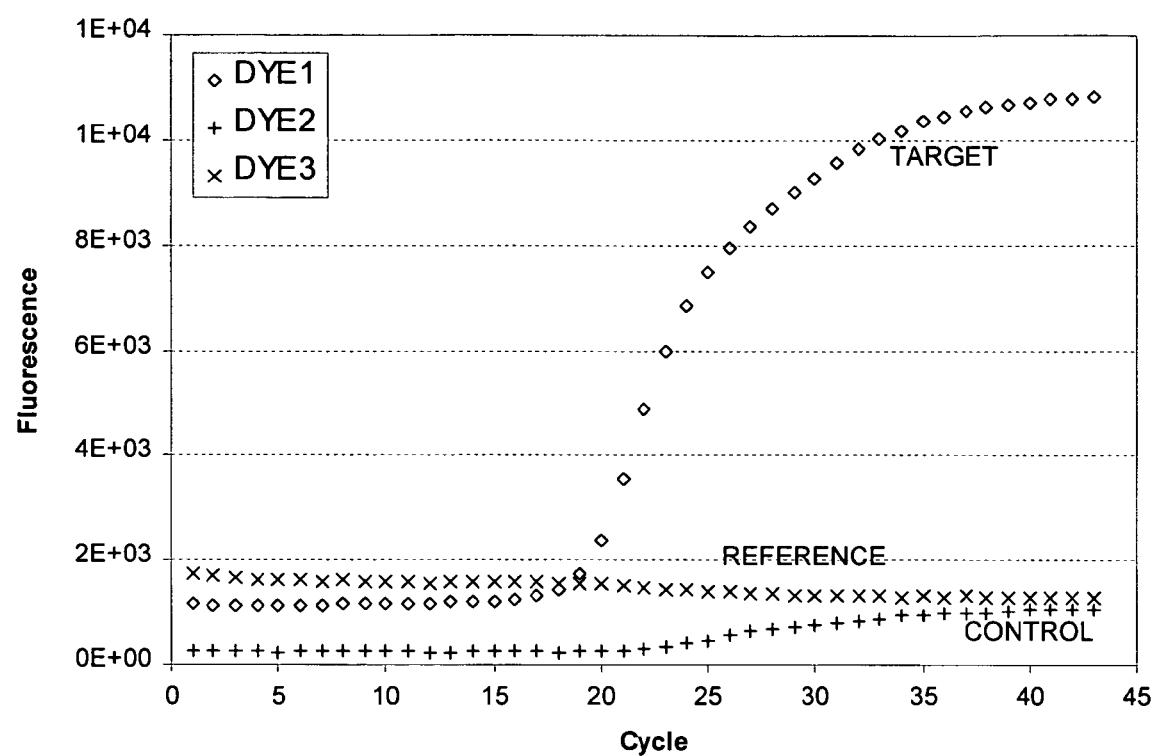
FIG. 1 is a plot of discrete captured reaction data values from 43 readings (e.g., cycles) taken from a nucleic acid amplification reaction that can be used in an analysis method according to embodiments of this invention.

As used herein, the expression "efficiency related value" means a value that has a consistent relationship to the efficiency of an amplification reaction. The expression "efficiency related transform" means a mathematical transformation involving the response in an amplification reaction that is used to determine an efficiency related value. The expression "reaction point" means a point during a reaction at which an efficiency related value occurs. The reaction point can be a point in time measured from the beginning of the reaction. Alternatively, the reaction point can be a point that denotes a cycle measured from the beginning of the reaction. The term "derivative" means the slope of a curve at a given point in the curve.

The present invention is directed to the analysis of a sample containing an analyte. The analyte can be a nucleic acid. In the context of the present invention, copies of a portion of the analyte are made (hereinafter "amplified") in a manner that generates a detectable signal during amplification. The signal is indicative of the progress of the amplification reaction, and preferably is related either to the quantity of analyte and copies of the analyte present in a test sample, or is related to the quantity of the copies of the analyte produced by the reaction. The amplification is preferably configured to allow logarithmic accumulation of the target analyte (e.g., as in a PCR reaction), and in a more preferred embodiment, the amplification is a PCR reaction in which data are collected at regular time intervals and/or at a particular point in each PCR cycle.

Many systems have been developed that are capable of amplifying and detecting nucleic acids. Similarly, many systems employ signal amplification to allow the determination of quantities of nucleic acids that would otherwise be below the limits of detection. The present invention can utilize any of these systems, provided that a signal indicative of the presence of a nucleic acid or of the amplification of copies of the nucleic acid can be measured in a time-dependent or cycle-dependent manner. Some preferred nucleic acid detection systems that are useful in the context of the present invention include, but are not limited to, PCR, LCR, 3SR, NASBA, TMA, and SDA.

Polymerase Chain Reaction (PCR) is well-known in the art and is essentially described in Saiki et al., *Science* 230; 1350-1354 (1985); Saiki et al., *Science* 239:487-491 (1988); Livak et al., U.S. Pat. Nos. 5,538,848; 5,723,591; and 5,876,930, and other references. PCR can also be used in conjunction with reverse transcriptase (RT) and/or certain multifunctional DNA polymerases to transform an RNA molecule into a DNA copy, thereby allowing the use of RNA molecules as substrates for PCR amplification by DNA polymerase. Myers et al. *Biochem.* 30: 7661-7666 (1991)

Ligation chain reactions (LCR) are similar to PCR with the major distinguishing feature that, in LCR, ligation instead of polymerization is used to amplify target sequences. LCR is described inter alia in Backman et al., European Patent 320 308; Landegren et al., *Science* 241:1077 (1988); Wu et al., *Genomics* 4:560 (1989). In some advanced forms of LCR, specificity can be increased by providing a gap between the oligonucleotides, which gaps must be filled in by template-dependent polymerization. This can be especially advantageous if all four dNTPs are not needed to fill the gaps between the oligonucleotide probes and all four dNTPS are not supplied in the amplification reagents. Similarly, rolling circle amplification (RCA) is described by Lisby, *Mol. Biotechnol.* 12(1):75-99 (1999)), Hatch et al., *Genet. Anal.* 15(2):35-40 (1999) and others, and is useful in the context of the present invention.

Isothermal amplification reactions are also known in the art and useful in the context of the present invention. Examples of isothermal amplification reactions include 3SR as described by Kwoh et al., *Proc. Nat. Acad. Sci.* (USA) 86: 1173-1177 (1989) and further developed in the art; NASBA as described by Kievits et al., *J. Virol. Methods* 35:273-286 (1991) and further developed in the art; and Strand Displacement Amplification (SDA) method as initially described by Walker et al., *Proc. Nat. Acad. Sci.* (USA) 89:392-396 (1992) and U.S. Pat. No. 5,270,184 and further developed in the art.

Thus, many amplification or detection systems requiring only that signal gains indicative of the quantity of a target nucleic acid can be measured in a time-dependent or cycle-dependent manner are useful in the context of the present invention. Other systems having these characteristics are known to the skilled artisan, and even though not discussed above, are useful in the context of the present invention.

Analysis of the data collected from the amplification reaction can provide answers to one or more of the following questions:

(1) Was the target sequence found?
(2) If yes, what was the initial level or quantity of the target sequence?
(3) Is the result correct?
(4) Did the reaction series run correctly?
(5) Was there inhibition of the desired or expected reaction?
(6) Is the sample preparation recovery acceptable?
(7) Is the calibration to any reference data, if used, still valid?

According to some embodiments of this invention, one or more of these questions can be answered by identifying a region of interest (e.g., an FCN) and an efficiency related value (e.g., an MR) of a target and/or internal control reaction. In other embodiments, one or more of these questions can be answered by comparing such values to data sets herein referred to as criteria data, criteria curves, and/or criteria data sets. In additional embodiments, one or more of these questions can be answered by comparing such values obtained for an internal control, e.g., a $2^{nd}$ amplification control reaction, in the same reaction mixture as its criteria data. In still further embodiments, one or more of these questions can be answered by comparing such values obtained for the target reaction to such values obtained for an internal control reaction in the same reaction mixture as their respective criteria data.

For clarity, the invention will be illustrated with reference to real-time PCR reactions, which are one class of measuring and monitoring techniques of high interest in automated and manual systems for detecting and quantifying human nucleic acids, animal nucleic acids, plant nucleic acids, and nucleic acids of human, non-human animal, and plant pathogens. Real-time PCR is also well adapted to detection of bio-warfare agents and other living or viral organisms in the environment. Real-time PCR combines amplification of nucleic acid (NA) sequence targets with substantially simultaneous detection of the amplification product. Optionally, detection can be based on fluorescent probes or primers that are quenched or are activated depending on the presence of a target nucleic acid. The intensity of the fluorescence is dependent on the concentration or amount of the target sequence in a sample (assuming, of course, that the quantity of the target is above a minimal detectable limit and is less than any saturation limit). This quench/fluoresce capability of the probe allows for homogeneous assay conditions, i.e., all the reagents for both amplification and detection are added together in a reaction container, e.g., a single well in a multi-well reaction plate. Electronic detection systems, target-capture based systems, and aliquot-analysis systems and techniques are other forms of detection systems useful in the context of the present invention so long as a given system accumulates data indicative of the quantity of target present in a sample during various time points of a target amplification reaction.

In PCR reactions, the quantity of target nucleic acid doubles at each cycle until reagents become limiting or are exhausted, there is significant competition, an inadequate supply of reactants, or other factors that accumulate over the course of a reaction. At times during which a PCR reaction causes doubling (exactly) of the target in a particular cycle, the reaction is said to have an efficiency (e) of 1 (e.g., e=1). After numerous cycles, detectable quantities of the target can be created from very small and initially undetectable quantity of target. Typically, PCR cycling protocols consist of between around 30-50 cycles of amplification, but PCR reactions employing more or fewer cycles are known in the art and useful in the context of the present invention.

In the real-time PCR reactions described below to illustrate the present invention, the reaction mixture includes an appropriate reagent cocktail of oligonucleotide primers, fluorescent dye-labeled oligonucleotide probes capable of being quenched when not bound to a complementary target nucleic acid, amplification enzymes, deoxynucleotide triphosphates (dNTPs), and additional support reagents. Also, a second fluorescent dye-labeled oligonucleotide probe for detection of an amplifiable "control sequence" or "internal control" and a "reference dye", which optionally may be attached to an oligonucleotide that remains unamplified throughout a reaction series, can be added to the mixture for a real-time PCR reaction. Thus, some real-time PCR systems use a minimum of three fluorescent dyes in each sample or reaction container (e.g., a well). PCR systems using additional fluorescent probe(s) for the detection a second target nucleic acid are known in the art and are useful in the context of the present invention.

Systems that plot and display data for each of one, or possibly more, reactions (e.g., each well in a multi-well plate) are also useful in the context of the present inventions. These systems optionally calculate values representing the fluorescence intensity of the probe as a function of time or cycle number ($C_N$) or both as a two-dimensional plot (y versus x). Thus, the plotted fluorescence intensity can optionally represent a calculation from multiple dyes (e.g., the probe dye and/or the control dye normalized by the reference dye) and can include subtraction of a calculated background signal. In PCR systems, such a plot is generally referred to as a PCR amplification curve and the data plotted can be referred to as the PCR amplification data.

In PCR, data analysis can be made difficult by a number of factors. Accordingly, various steps can be performed to account for these factors. For example, captured light signals can be analyzed to account for imprecision in the light detection itself. Such imprecision can be caused by errors or difficulties in resolving the fluorescence of an individual dye among a plurality of dyes in mixture of dyes (described below as "bleedover"). Similarly, some amount of signal can be present (e.g., "background signal") and can increase even when no target is present (e.g., "baseline drift"). Thus, a number of techniques for removing the background signal, preferably including the baseline drift, trend analysis, and normalization are described herein and/or are known in the art. These techniques are useful but are not required in the context of the present invention. (Baseline drift or trending can be caused by many sources, such as, for example, dye instability, lamp instability, temperature fluctuations, optical alignment, sensor stability, or combinations of the foregoing. Because of these factors and other noise factors, automated methods of identifying and correcting the baseline region are prone to errors.)

Typically in PCR, the answers of interest are generally determined from a growth curve, which characteristically starts out as nearly flat during the early reaction cycles when insufficient doubling has occurred to cause a detectable signal, and then rises exponentially until one or more reaction limiting conditions, such as exhaustion of one or more reactants, begins to influence the amplification reaction or the detection process.

A number of methods have been proposed and have been used in research and other settings to analyze PCR-type reaction data. Typically, these methods attempt to detect when the reaction curve has reached a particular point, generally during a period of exponential or near-exponential signal growth (also known as "the log-linear phase"). While not wishing to be bound by any theory, the inventors believe that the earliest point(s) in which the log linear phase can be observed above the baseline or background signal provides the most useful information about the reaction and that the slope of the log-linear phase is a reflection of the amplification efficiency. Some prior art references erroneously suggest that for the slope to be an indicator of real amplification (rather than signal drift), there has to be an inflection point, which is the point on the growth curve where the log-linear phase ends. The inflection point can also represent the greatest rate of change along the growth curve. In some reactions where inhibition occurs, the end of the exponential growth phase may occur before the signal emerges from the background.

In running a PCR analysis, it is generally desired to determine one or more assay results regarding the initial amount/concentration of the target molecules. For discussion purposes, results may be expressed by answers to at least one of four questions:

(1) Was the target molecule present at all in the initial sample (e.g., a positive/negative detection result)?
(2) What was the absolute quantity of the initial target present?
(3) What is the confidence (e.g., sometimes expressed as a confidence value that the answers to questions 1 or 2 are correct)?
(4) What is the relative amount of the target present in two different samples?

A number of methods have been proposed and can be used in research and other settings to answer one or more of these questions.

Data for PCR reactions is often collected one time in each cycle for each dye that is measured (i.e., fluorescence determined) in a reaction. While such data is useful in the context of the present invention, more precise quantification can be carried out by interpolation between the data points acquired at each cycle. In this way, the data can be analyzed to generate "fractional cycle numbers", and points of interest can be determined to be coincident with a particular cycle number or at a reaction point between any pair of cycle numbers.

One problem with methods that rely on thresholds, particularly in diagnostic settings where it is desirable to fix thresholds, is that theses methods can be susceptible to errors due to the presence of noise factors, particularly systematic noise factors, such as, for example, "crosstalk" and "bleedover". Crosstalk can generally be understood as occurring when a signal from an assay in one location (such as one well in a multi-well plate) causes an anomaly in a signal in a different, usually adjacent assay location. Bleedover can generally be understood as occurring in situations where more than one signal or data set is detected from the reaction. While detection dyes for a reaction are selected to be largely independent from each other and to have individual fluorescence emission spectra, the emission spectra sometimes overlap such that the emission spectrum from one dye will bleedover into the emission spectrum of a different dye.

Both crosstalk and bleedover can have the effect of either increasing or decreasing the calculated measurement of interest. Furthermore, in both cases, there can be situations where the curve itself can have an anomaly due to either or both of these phenomena. Systematic noise factors such as crosstalk and bleedover can be especially difficult to deal with when performing a baseline correction.

In some systems of the prior art, in order to detect low-level signals for either qualitative results or quantitative results, a low threshold is generally required. However, the use of a low threshold causes discrimination between a false positive signal due to crosstalk and a correct positive signal to be particularly difficult, because either can cause the PCR curve to rise above an amplification threshold, thereby suggesting that a target analyte is present. Positive and negative bleedover can also present problems. Positive bleedover can produce a false-positive results or cause falsely elevated estimates of the initial quantity of target in a sample, while negative bleedover can cause falsely depressed estimates of the initial quantity of target in a sample or falsely indicate the absence of a target in a test sample.

The method or system of this invention can reproducibly identify a region in a reaction curve or data, preferably using an information processing system, which can then be used to provide results based on the amplification reaction data. The invention can identify this region regardless of the base level of the signal, even in the presence of substantial noise. The invention can furthermore identify a value that is representative of efficiency at that region. This value can be used in determining primary results or in adjusting results or in determining confidence values as described herein, or all of the foregoing.

The invention can be illustrated by a specific example, shown below. In this example, an information processing system is used to analyze data representing the growth curve of an amplification reaction. In the amplification, a "peak" is generated by one step in the data analysis. The location of this peak (measured in time units or in cycles from the initiation of the amplification reaction) is referred to as the fractional cycle number (FCN) and the maximum value of the peak is referred to as the ERV (efficiency related value). These values can be used in a method to identify an efficiency related value region and to determine an efficiency related value at this peak. Both of these values can be understood as being derived from a method that analyzes the shape of the reaction curve regardless of the intensity of the amplification signal, which intensity of amplification signal can vary from reaction to reaction and from instrument to instrument, despite starting with identical samples. The reaction curve is a representation of the reaction wherein a signal substantially indicative of the quantity of target in a reaction is plotted as a function of time or, when appropriate, cycle number. The FCN can be understood as being consistently related to a point of maximum growth efficiency of a reaction curve, and the ERV can be understood as being consistently related to the efficiency at that point.

In some embodiments of this invention, analytical methods can optionally, and advantageously, be employed without use of baseline correction. In some systems and methods of this invention, a reference dye is not needed.

The present invention allows objective quantification of the quantity of a target present in a test sample without the need to calculate a subjective and variable threshold or a $C_t$ value, as employed in some techniques of the prior art. Furthermore, the invention can use information that is available for determining the degree of inhibition in a reaction by analyzing the shape of the PCR amplification curve, including data that previously has generally been ignored, such as data in cycles after a $C_t$.

General methods for generating and using data pairs determined from reaction curve data will be understood from the examples below. For clarity, these examples refer to a specific set of data and specific functions for analyzing that data, though the invention is not limited to the examples discussed.

EXAMPLE 1

Captured Data

By way of example, a typical real-time PCR reaction detection system generates a data file that stores the signal generated from one or more detection dyes. FIG. 1 illustrates a plot of captured reaction data that can be used in an analytical method according to the present invention. In this example, one dye signal (DYE1) provides the captured target data, another dye signal (DYE2) provides captured internal control data, and a further dye signal (DYE3) provides optional captured reference data. These data represent data from a single reaction, taken from a standard output file. This particular plot can be understood to represent initial data to which some type of multi-component algorithm has been applied. In this plot, the x-axis provides an indication of cycle number (e.g., 1 to 45) and the y-axis indicates dye intensity detected, in relative fluorescence units. In this figure, the three different capture data sets are illustrated as continuous curves. However, the actual captured data values are generally discrete signal values captured at each cycle number. Thus, an initial data set as illustrated in FIG. 1 may consist of three sets (target, control, and reference) of suitable discrete values (e.g., about 50 values in this case).

EXAMPLE 2

Normalization

Figure 2:
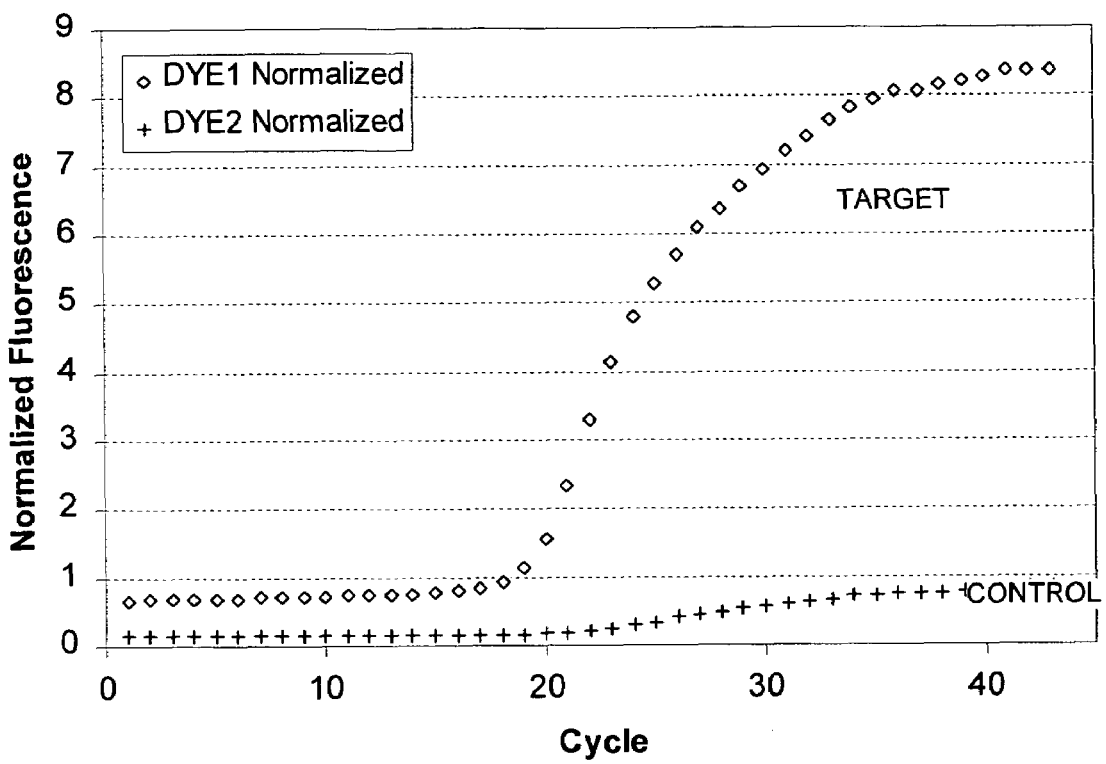
FIG. 2 is a plot illustrating captured reaction data showing target and control data sets that have been normalized according to embodiments of this invention.

Although optional, normalization can be performed on the captured data in several different ways. One method involves dividing the target and control values at each cycle reading by the corresponding reference dye signal. Alternatively, the divisor can be the average reference value over all cycles or an average over certain cycles. In another alternative embodiment, the divisor can be the average of the target dye or the control dye or the target dye and the control dye over one or more earlier (baseline) cycles, when no amplification signal is detected. Any known normalization method can be employed in a data analysis. The invention can be used with data that has already been normalized by a PCR system. FIG. 2 is a plot of captured reaction data showing target and control data sets that have been normalized according to the present invention. In this example, as a result of the normalization, the y-axis scale represents a pure number. In this case, the number is between about 0 and 9. Other normalization methods are known in the art and can convert this number to between about 0 and 100 or to any other desired range.

Because normalization is optional, the present invention can be used to analyze reaction data without the use of a normalization or reference dye. Alternatively, the target signal or the control signal or both can be used for normalization.

EXAMPLE 3

Scaling

Scaling is optional but can be performed to make it easier for a human operator to visualize the data. Scaling does not affect analytical results. Scaling can be carried out in addition to normalization, in the absence of normalization, or before or after normalization.

Figure 3:
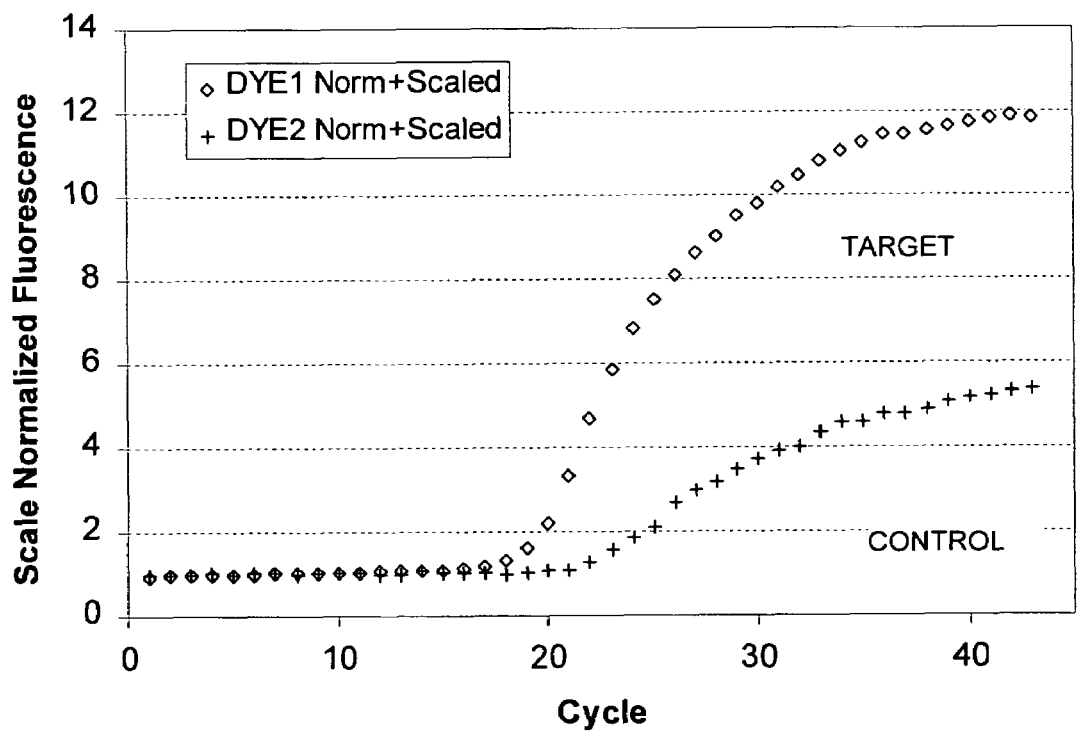
FIG. 3 is a plot illustrating reaction data showing target and control data that have been scaled according to embodiments of this invention.

One method of scaling involves dividing each data set value by the average of the values during some early cycles, generally in the baseline region before any positive data signal is detected. In this example, readings 4 through 8 were averaged and normalization was performed first. FIG. 3 is a plot of reaction data showing target and control data that have been scaled. In this example, scaling forces the early values of the target and control to one, and because the early values are less than one, the division forces the later values to slightly larger pure numbers.

EXAMPLE 4

Digital Filtering

Figure 4:
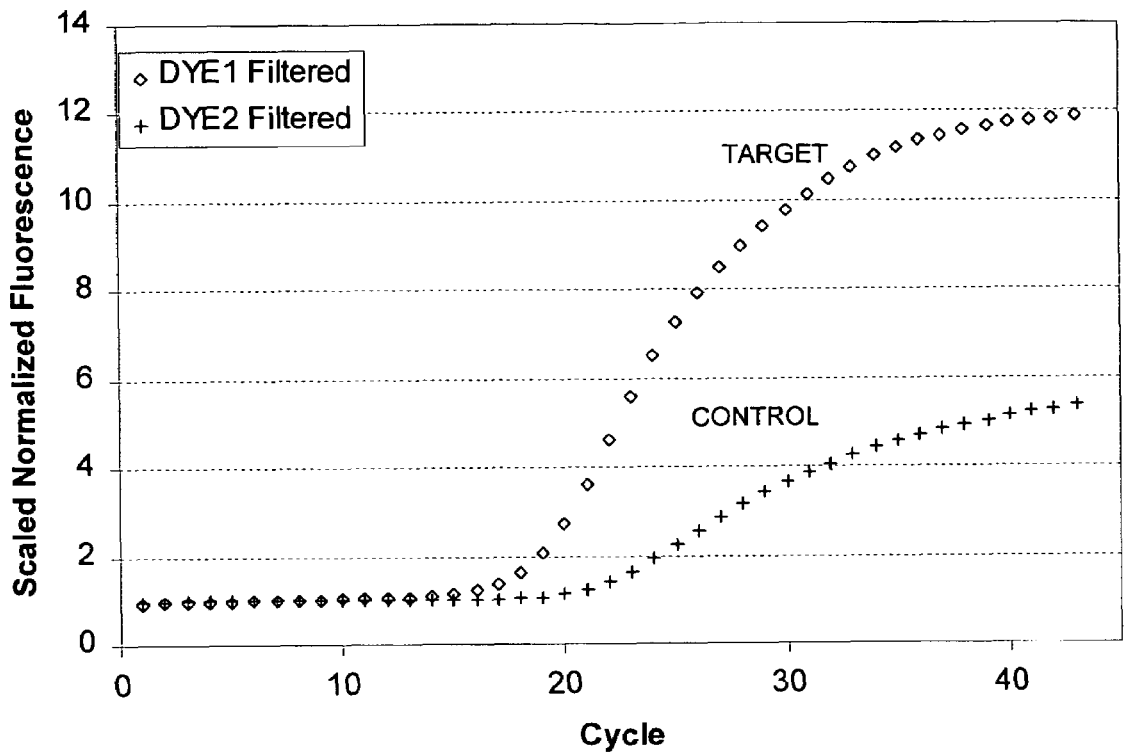
FIG. 4 is a plot illustrating captured reaction data showing target and control data after digital filtering according to embodiments of this invention.

One or more digital filtering methods can be applied to the captured data to "clean up" the signal data sets and to improve the signal to noise ratio. Many different filtering algorithms are known. The present invention can employ a four-pole filter with no zeros. This eliminates the potential for overshoot of the filtered signal. As an example, this can be implemented with the MATLAB function "filtfilt" provided with the MATLAB Signal Processing Toolbox, which both forward and backward filters to eliminate any phase lag (time delays). An example of parameters and MATLAB function call is as follows:

b=0.3164;
a=[1.0000 −1.0000 0.3750 −0.0625 0.0039];
data(:,:,assay)=filtfilt(b,a,data(:,: ,assay));
data(:,:,ic)=filtfilt(b,a,data(:,:,ic));

In this example, "b" and "a" contain the filter coefficients. "data(:,:,assay)" and "data(:,:,ic)" contain the captured data that may or may not have been normalized, scaled, or both. In this case, the filtered data is both normalized and scaled. FIG. 4 is a plot of captured reaction data showing target and control data after digital filtering. The values are not changed by the digital filtering, but the data set is "smoothed" somewhat.

EXAMPLE 5

Slope Removal/Baselining

Figure 5:
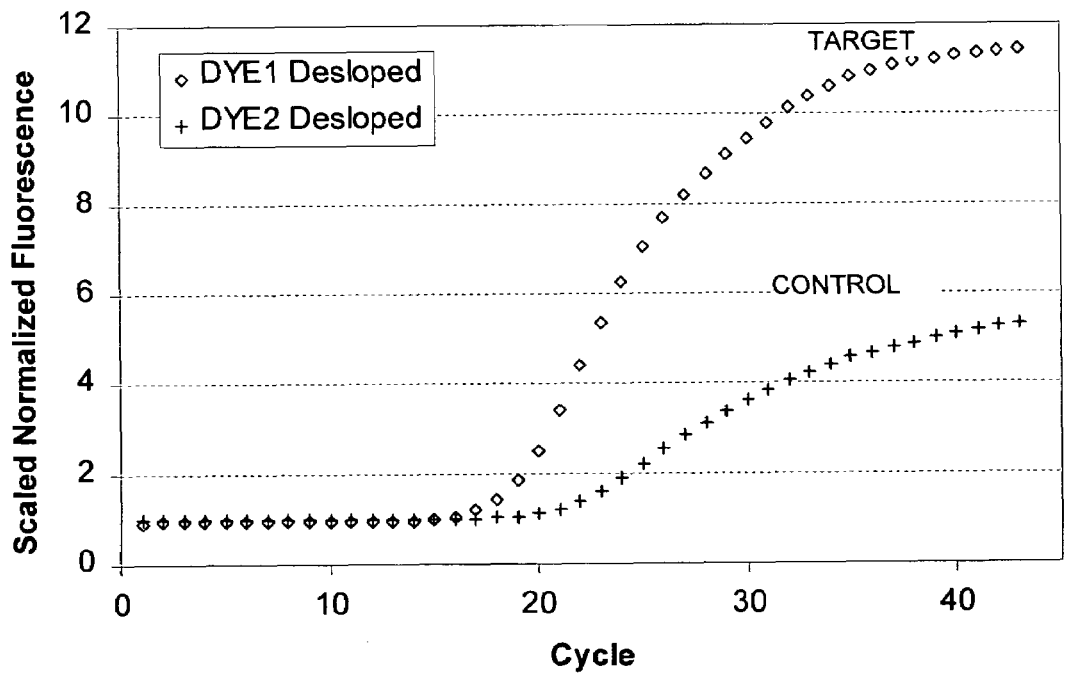
FIG. 5 is a plot illustrating captured reaction data showing target and control data with slope values removed according to embodiments of this invention.

An optional slope removal method can be used to remove any residual slope that is present in the early baseline signal before any detectable actual signal is produced. This procedure may also be referred to as baselining, but in some embodiments, the offset is not removed, only the slope. According to this invention, for slope removal, both the target (DYE1) and control (DYE2) signals are examined simultaneously. Whichever signal comes up first defines the forward regression point, and the method generally goes back 10 cycles. If 10 cycles back is before cycle 5, then cycle 5 is used as the initial regression point to avoid any earlier signal transients. A linear regression line is calculated using the signal data between these points and the slope of the regression for each dye is subtracted from that dye's signal. In this case, the slope removal is applied to the normalized, scaled, and filtered data discussed above. FIG. 5 is a plot of captured reaction data showing target and control data with slope values removed. In each of these figures, very little slope was present in early cycles; therefore, the slope removal does not substantially affect the captured data values.

EXAMPLE 6

Transform Calculation

An embodiment of the method of this invention is the MaxRatio method. In this method, the ratio between sequential measurements is calculated, thereby yielding a series of ratios, each of which can be indexed to a time value or cycle number. Many suitable means of calculating these ratios exist, and any suitable means can be used. The simplest way of performing this ratio calculation utilizes the following function:

$$\text{Ratio}(n) = \frac{s(n+1)}{s(n)}$$

where n represents the cycle number and s(n) represents the signal at cycle n. This calculation provides a curve that starts at approximately 1 in the baseline region of the response, increases to a maximum during the growth region, and returns to approximately 1 in the plateau region. A MATLAB expression that performs this calculation efficiently is the following:

Ratio=$s$(2:end,:)./$s$(1:end−1,:), where "s" represents the signal response matrix, with each column representing a separate response.

Figure 6:
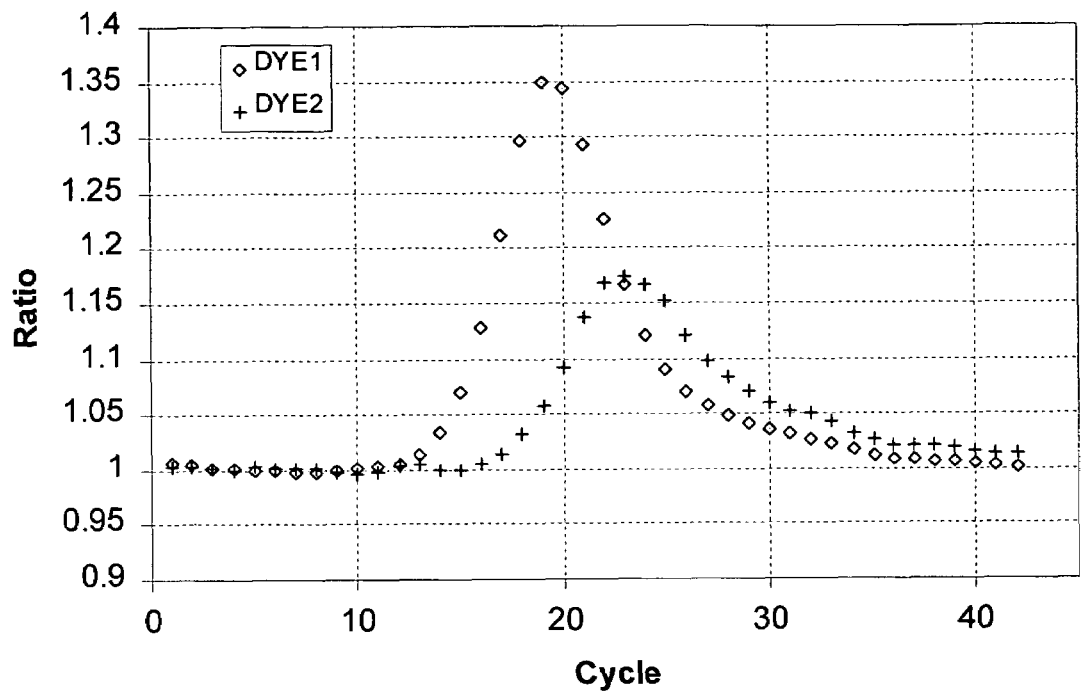
FIG. 6 is a plot illustrating ratio transform of reaction target and control data according to embodiments of this invention.

FIG. 6 shows an example of this ratio transform. Because of the intrinsic background fluorescence, the ratio does not reach 2 as would be expected of a PCR reaction if the signal were doubling. Regardless, the magnitude of the peak is independent of multiplicative intensity variations and is proportional to the rate of growth or efficiency at that point. The method of calculating ratios is simple and efficiently calculated. Other equivalent calculations could be made. An example would involve calculating the forward and reverse ratios and then averaging them. On can use the inverse of the ratio, in which case the curve will begin at a value of approximately 1 in the baseline region, decrease in the growth region, and return to a value of approximately 1 in the plateau region. One would then use the magnitude and location of the trough instead of a peak for analysis. This transform can be implemented in a manner essentially equivalent to the ratio method.

Although the MaxRatio algorithm is usable as described, it is convenient to shift the curve by subtracting a constant, e.g., about one (1), from each point. This operation provides a transformation of the original response, which starts near zero in the baseline region, rises to a peak in the growth region of the curve, and returns near zero in the plateau region. This shifted ratio calculation is described by the following function:

$$\text{Ratio}(n) = \frac{s(n+1)}{s(n)} - 1.$$

Figure 7:
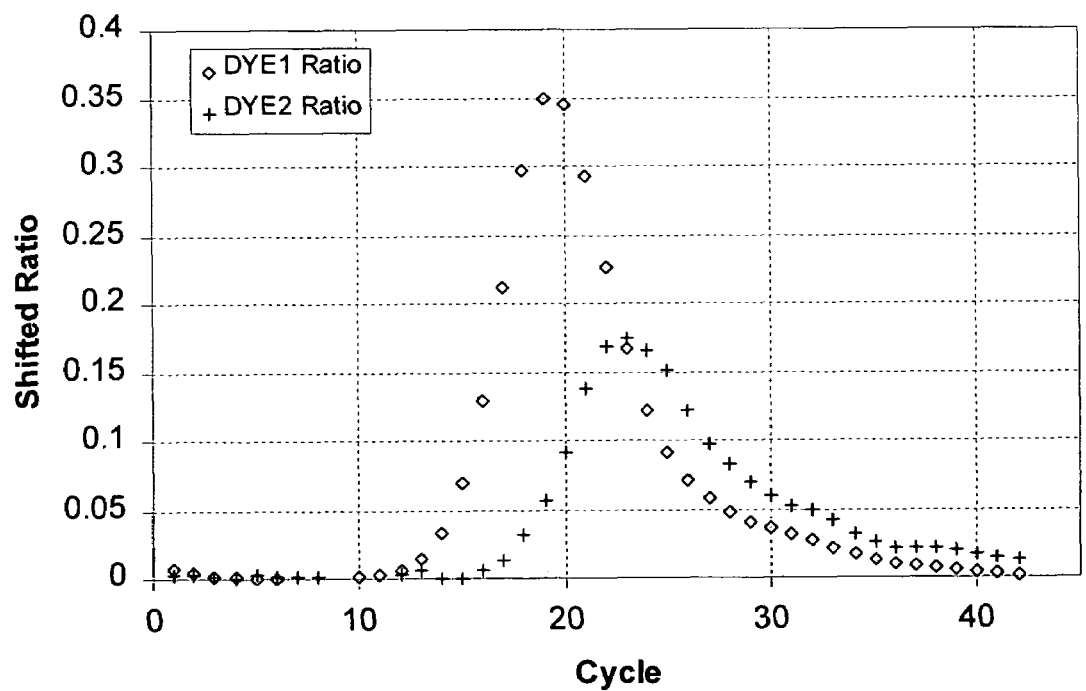
FIG. 7 is a plot illustrating shifted ratio transform of reaction target and control data according to embodiments of this invention.

FIG. 7 shows the output of this shifted ratio calculation. The reaction point and magnitude of the peak of the shifted ratio curve is then determined. The reaction point (i.e., distance along the x-axis) specifies the FCN value of the MR and the magnitude specifies the efficiency related value MR (Maximum of the Ratio).

EXAMPLE 7

Interpolation

In order to enhance cycle number resolution, an interpolation can be performed. Many ways of accomplishing this operation are known in the art. One method of interpolating in the context of the invention is cubic spline interpolation, which provides a smooth interpolation, so that even the second derivative of the captured data sets will be continuous. The invention can be used to interpolate the entire data' series. The invention can be used to determine a region of interest and then to interpolate only in that region to achieve sub-periodic, or sub-cycle, resolution. An example of a MATLAB command for performing a cubic spline interpolation is as follows:

```
out=interp1(x,in,x2,'spline')
``` where "x" represents the period (or cycle) numbers (1,2, 3 . . . ), "in" represents the uninterpolated signal at those cycles, "x2" represents the higher resolution period (or cycle) vector (1.00, 1.01, 1.02, . . . ) and "out" represents the interpolated signal that corresponds to the fractional cycles in "x2".

Figure 8:
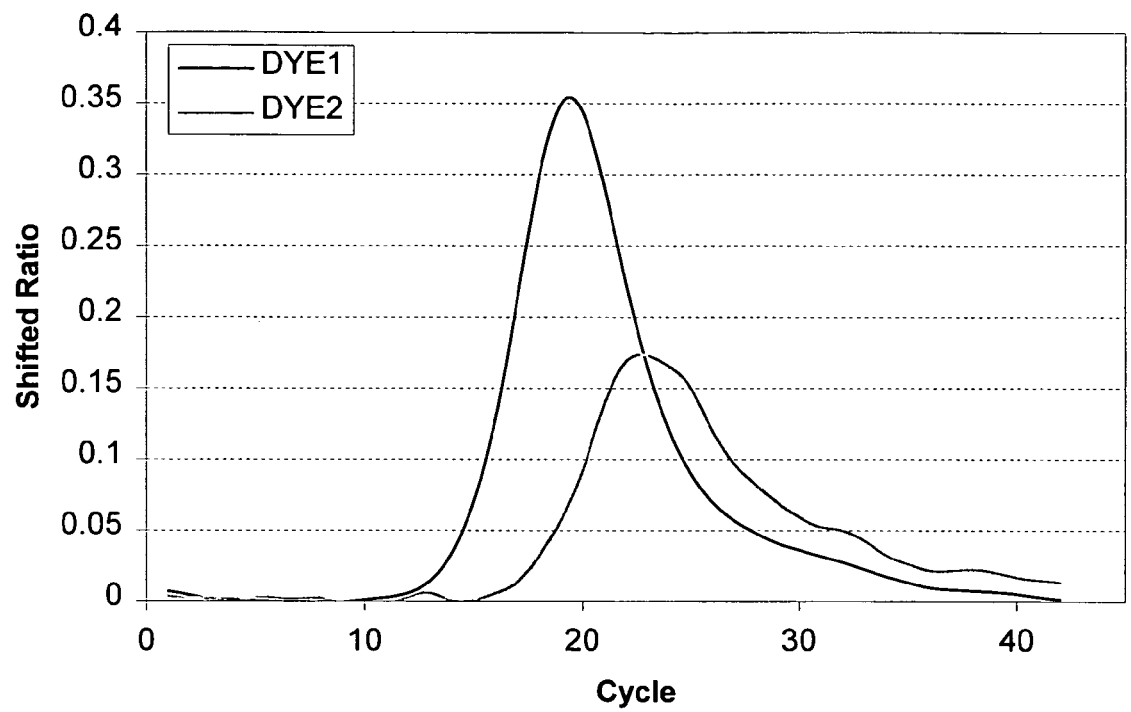
FIG. 8 is a plot illustrating interpolated transformed reaction data showing target and control data that have been interpolated according to embodiments of this invention.

FIG. 8 is a plot of captured reaction data showing target and control data that have been interpolated to provide function continuity. As a result of an interpolation, the number of values in the data set will generally increase substantially, for example from 43 values to 4201 values.

It should be understood that the steps described above can be performed in different orders, such as, for example, filtering first, followed by baselining before scaling. However, if the interpolation is performed before the ratio calculation, care must be taken to select the appropriate interpolated response values for the ratio calculation. It is important that the interval between ratio values remain the same. Thus, if cycles are used as the period of measurement, and interpolation increases the time resolution to 0.01 cycles, then the shifted ratio at x=2.35 would be R=s(3.35)/s(2.35)−1.

EXAMPLE 8

Finding Peaks to Determine FCN and ERV (e.g., MR) of Target and Control

Another step is to select peaks in the data series. This operation involves the steps of (1) finding local peaks and (2) selecting from local peaks one or more peaks for further analysis, optionally using criteria data (defined infra).

A peak-finding algorithm identifies where the slope of the curve changes from positive to negative, which represents a local maximum. The algorithm identifies the locations and the magnitude of the peaks. An example of a MATLAB function to do this calculation is as follows:

```
function [ind,peaks]=findpeaks(y)
```

% FINDPEAKS Find peaks in real vector.
% ind=findpeaks(y) finds the indices (ind) which are
% local maxima in the sequence y.
% [ind,peaks]=findpeaks(y) returns the value of the
% peaks at these locations, i.e. peaks=y(ind);

```
y = y(:)';
switch length(y)
  case 0
    ind = [ ];
  case 1
    ind = 1;
  otherwise
    dy = diff(y);
    not_plateau_ind = find(dy~=0);
    ind = find( ([dy(not_plateau_ind) 0]<0) &
       ([0 dy(not_plateau_ind)]>0) );
    ind = not_plateau_ind(ind);
end
if nargout > 1
  peaks = y(ind);
end
```

Figure 9:
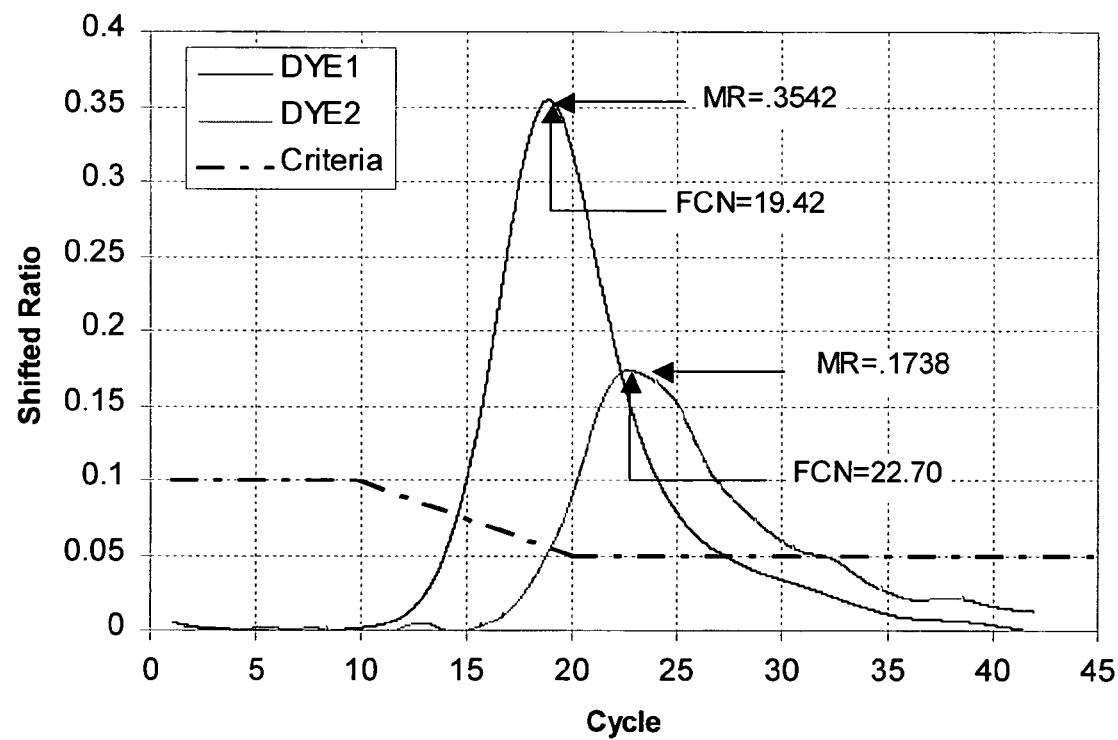
FIG. 9 is a plot illustrating interposed reaction data showing identification of the FCN and MR points according to embodiments of this invention.

FIG. 9 is a plot of an efficiency calculation showing identified FCN and MR values of the target and internal control dyes and a criterion curve according to embodiments of the present invention. For the target data, FINDPEAKS located one peak at cycle axis x=19.42 with a magnitude of 0.354. For the internal control data, FINDPEAKS found peaks at: x=2.03, 5.29, 7.67, 12.83, 22.70, 37.86, with respective magnitudes 0.0027, 0.0027, 0.0022, 0.0058, 0.1738, 0.0222.

EXAMPLE 9

Selecting Peaks to Determine FCN and ERV (e.g., MR) of Target and Control

In the method discussed above, a number of local maximum peaks are often identified for both the target data and the control data. Various methods can be used for selecting which of these local maximum peaks will be used for determining an FCN and ERV.

Typically, and in particular during well-behaved reactions, the highest peak or maximum peak is selected. In many situations, this selection provides the most reproducible reaction point from which to perform further calculations as discussed herein. However, in some situations, a first peak, or first peak above a particular cutoff or after a particular number of cycles is preferable. Thus, in particular examples, a Max Peak or First Peak selection can be employed where Max Peak finds the largest peak in the shifted ratio curve while First Peak finds the first peak that is higher than some selected value.

Once criteria data are determined, these data can also be used to determine which peak to select for an ERV determination during actual operation, particularly for weak or noisy signals.

In FIG. 9, for example, for the DYE2 data, the peak-finding algorithm found six local peaks, but the fifth peak was the maximum peak and was also the only one that was above the criterion curve. Thus, in this example, an FCN determined for DYE2 is 22.70 and the MR determined for DYE 2 is 0.1738.

Figure 10:
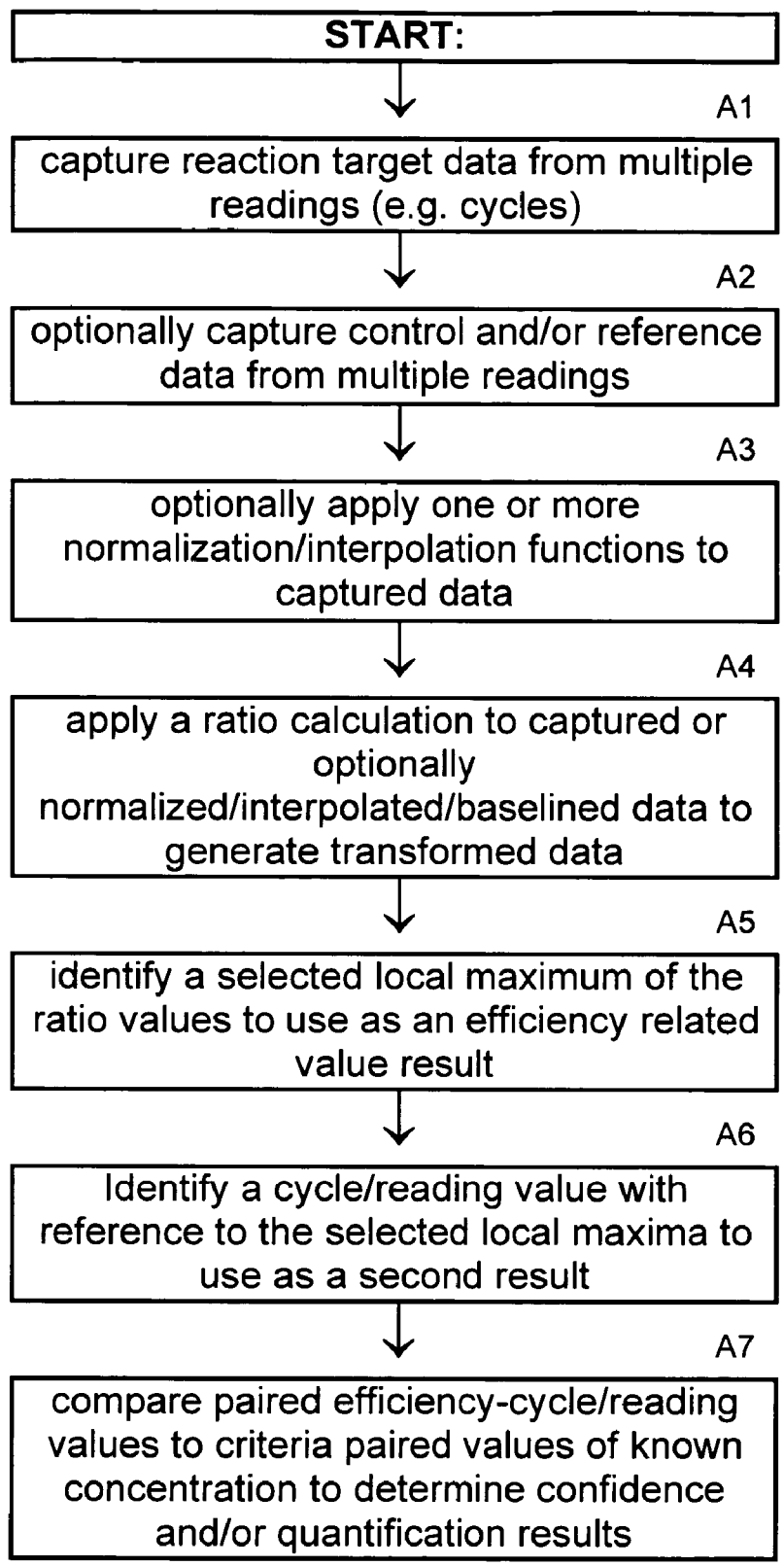
FIG. 10 is a flow chart for performing a characterization of reaction data according to embodiments of this invention.

An information appliance or system apparatus can also be used to perform the methods of this invention. FIG. 10 is a flow chart for performing a reaction data characterization according to embodiments of the present invention. Further details of this general method will be understood from the discussion below.

The analytic methods described herein can be applied to reactions containing either known or unknown target concentrations. In one embodiment, known target nucleic acid concentrations will be included in calibration wells in a reaction carried out in a multi-well reaction plate, and the ERV and value of the reaction point will be used from these known concentration samples to perform quantification. Known concentrations may also be used to develop criteria data as further described herein.

EXAMPLE 10

Determining Criteria Curve/Criteria Data Sets

In other embodiments, efficiency related values (e.g., MR values) can be plotted as a function of their reaction point values (FCN values) for a number of data sets of known concentration in order to generate a characteristic criterion curve for a particular assay. The criterion curve is characteristic of a particular assay formulation and detection protocol and can be used to reliably determine positive/negative results, to determine whether a particular result should be discarded as unreliable, to determine a confidence measure of a result, or any combination of the foregoing. In general, pairs of reaction data that lie below a criterion curve indicate non-reactive samples, or non-functional reactions, such as reactions encountering significant inhibition.

Criteria data can be used to select which peaks to report or to use in reaction analysis, or both. Criteria data provide an automatic and reliable method for discriminating between negative results (e.g., target not present at all) and results showing low amount of target.

Figure 11:
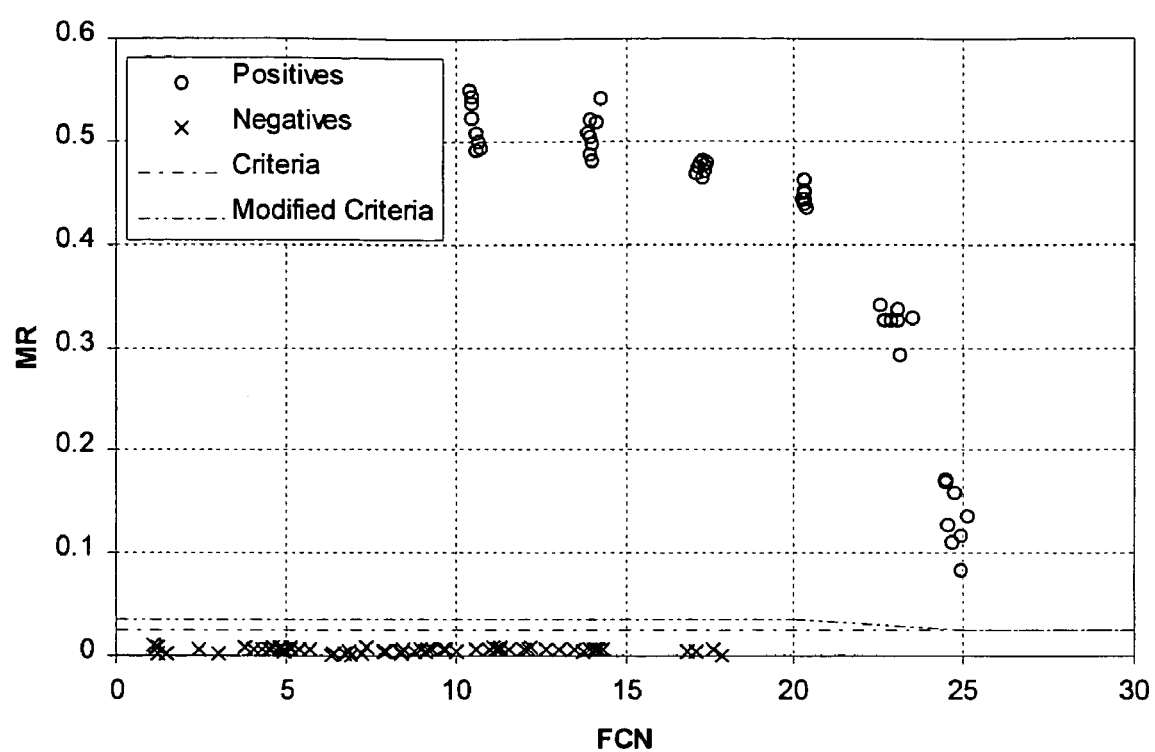
FIG. 11 is a plot illustrating methods for determining criteria data according to embodiments of this invention.

FIG. 11 is a plot in which the MR of six sets of reactions of known concentration (i.e., standards or calibrators) and one set of negative reactions are plotted as a function of the calculated FCN value of the MR value. This plot allows a criterion curve to be selected. A criterion curve, which was described previously, is any curve or line that separates positive results from negative results. The criterion curve is preferably selected so that it is relatively close to and above the negative reaction data (in the x-y space of the plot). In FIG. 11, pairs of MR-FCN data from a number of samples of known concentrations determined under the same or similar assay conditions are plotted together with pairs of MR-FCN data from samples that do not contain the target of the assay, which samples are also referred to as negatives. Although the negatives should exhibit no amplification response, the analytical method does determine an MR-FCN data pair for these samples. These data for negative samples usually correspond to noise driven maxima on the response output, which is generally a random response. The MR value determined from noise is very low and far removed from the responses from samples of known concentrations. MR-FCN pairs for negative reactions can cluster if there is a systematic noise source, such as bleedover, in which case the MR-FCN pairs may falsely appear to be positive reaction signals. In characterizing the MR-FCN response of true positives versus true negatives, one can identify a clear region of separation between these two sets of data, which is represented by the broken line or curve in FIG. 11, the criterion curve. In this figure, each circle represents a FCN-MR data pair. In this case, each of the clusters of circles represents multiple responses at known concentrations of the target. There are eight different replicates at six known concentrations within this example. From the right of the plot, for example, these known concentrations can represent concentrations of 50 copies/ml, $5\times10^2$ copies/ml, $5\times10^3$ copies/ml, $4\times10^4$ copies/ml, $5\times10^5$ copies/ml, and $5\times10^6$ copies/ml. These criteria data clusters can be used to generate a criterion curve.

Multiple, relatively simple criteria data sets can be used to provide characteristic criteria curves for a number of assays. One useful approach involves taking the mean of the MR values for the set of negative responses and adding to this value a multiple of the standard deviation of the MR values for the negative responses. For the example shown in FIG. 11, the criterion curve was set to be a horizontal line equal to the mean plus 10 standard deviations of the MR values for the negative responses. The criterion value in this example was calculated to be about 0.026. In some systems, other considerations can make modification of the criterion value (e.g., an FCN-MR value) desirable to account for potential signal anomalies, such as, for example, crosstalk or positive bleedover. Crosstalk can result from signal in a positive well of a multi-well instrument and influence the signal from a different well. As much as 2% crosstalk has been observed in certain instruments. For this reason, the criterion may be increased so as to avoid classifying true negative samples as positive samples. For the assay data represented in FIG. 11, the highest MR values for positive assays are about 0.50. Two percent of this value is 0.010. Increasing the criterion by 0.010 should eliminate false positives due to crosstalk. Because the highest MR values in this assay only occur with samples of higher concentration that have smaller FCN values, the criterion may be increased only at smaller FCN values, where crosstalk is likely to occur. This modified criteria set can be described by a series of data pairs $(X_n, Y_n)$, which describe a multi-element curve. For example, the modified criterion curve shown in FIG. 11 can be specified by the criteria data set:

$(X_1, Y_1) = (1, 0.036)$ $(X_2, Y_2) = (20, 0.036)$ $(X_3, Y_3) = (25, 0.026)$ $(X_4, Y_4) = (45, 0.026)$

As a further example, the criterion curve shown in FIG. 10 can be specified by the criteria data set:

$(X_1, Y_1) = (1, 0.10)$ $(X_2, Y_2) = (10, 0.10)$ $(X_3, Y_3) = (20, 0.05)$ $(X_4, Y_4) = (40, 0.05)$

Criteria curves and/or criteria data sets, including sets having different shapes or more complex shapes or both, can be determined without undue experimentation. The intended use of the PCR application will call for different approaches to establishing criteria lines. The skilled artisan will readily appreciate that when high sensitivity is desired in an assay, a low criterion line is used. For example, if an assay is designed for differentiating sequence variants, such as population consensus sequence (i.e., a "wild type" sequence) versus polymorphic or variant sequences (e.g., a "single nucleotide polymorphism"), then a criterion line of higher value can be used, because the detection of limiting quantities of target nucleic acid is not usually required in the determination of sequence variants.

The particular example shown in FIG. 11 does not exhibit positive bleedover from the internal control (IC) signal response to the assay signal response. If positive IC signal response to assay bleedover were to be present, a similar modification to the criterion could be made. Because the IC signal response should only occur over a narrow range of EON values, the criterion could be increased only in that limited range.

Generally, as further discussed herein, a FCN-MR response is determined for samples of known concentration across the target concentration range of interest to define the "normal" response. Additional studies in a population of samples that challenge the assay reaction may be run to see how much deterioration in MR is acceptable before the assay performance is compromised. These types of characterization analyses can be used to establish criteria data or sets of criteria data independently of the standard deviation or other characteristics of the noise or baseline observed when samples that do not contain target nucleic acid are treated under amplification conditions.

According to other embodiments of the invention, criteria data also can be determined in ways similar to determining a $C_t$, for $C_t$ analysis as has been done in the prior art. A particular assay under design can be performed a number of times to characterize it's typical MR-FCN response. From this typical response, the criteria data set can be defined. However, unlike $C_t$ analysis, in FCN-MR, the response is independent of intensity of signal and is easily reproducible, even across instruments of a particular type that produce highly variable results with identical samples.

EXAMPLE 11

Alternative Region of Interest

Figure 12:
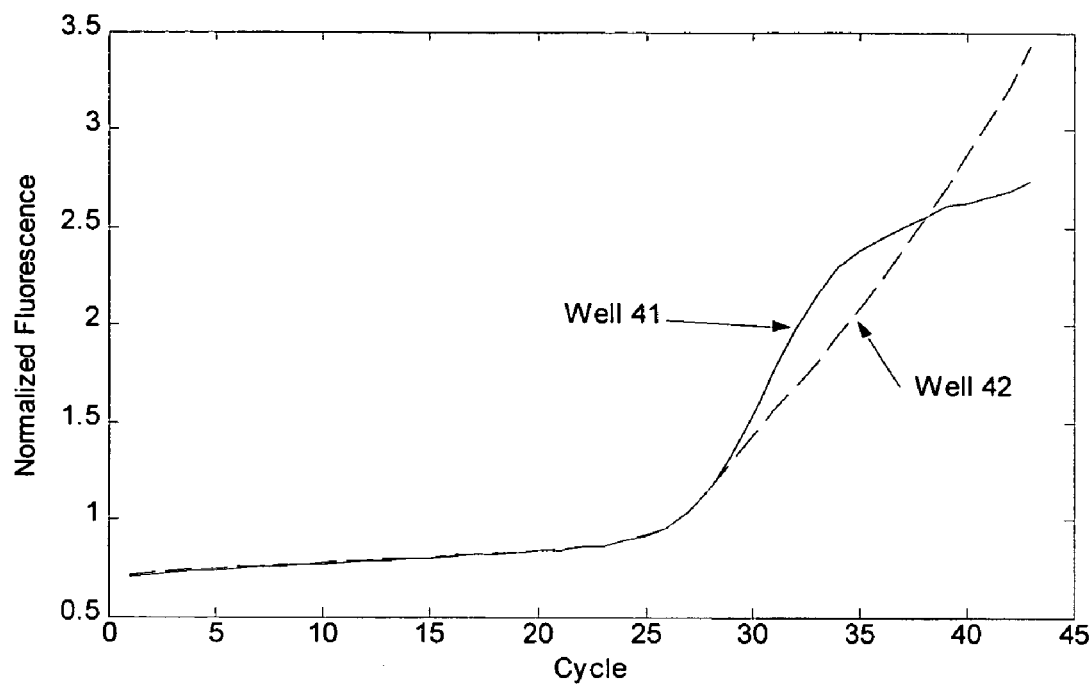
FIG. 12 is a plot illustrating two sets of reaction data that illustrate how reaction curves for same concentration initial samples can vary due to different reaction anomalies.
Figure 13:
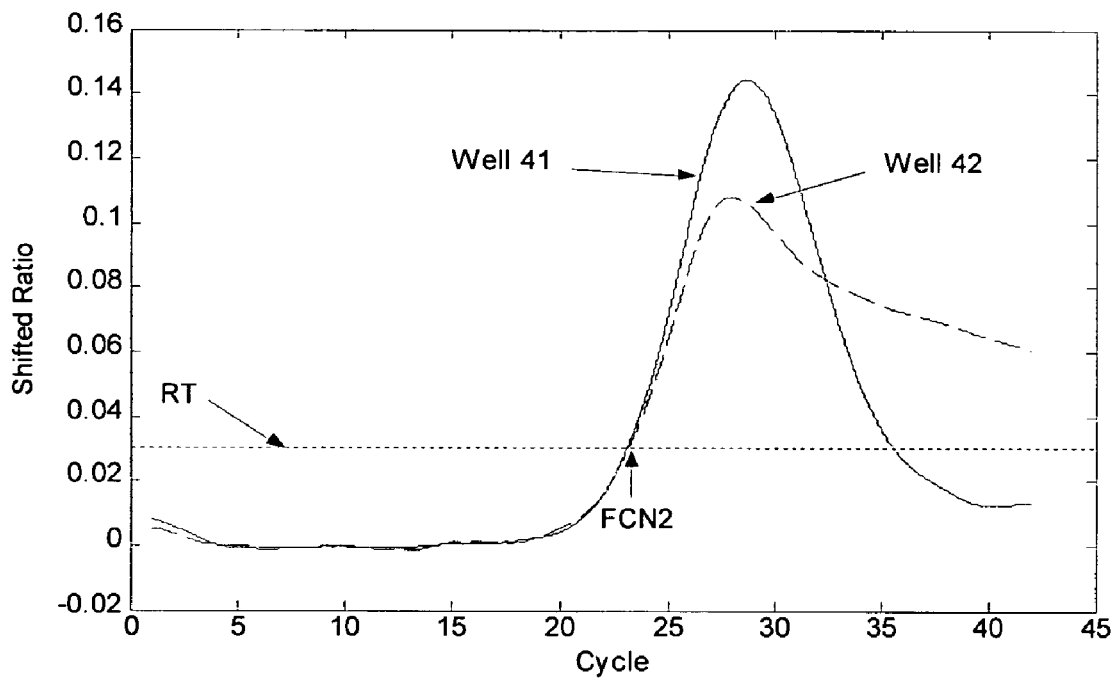
FIG. 13 illustrates peak efficiency calculations for the data sets in FIG. 12. The figure illustrates the desirability of using an offset efficiency transform according to specific embodiments of the present invention.

It has been empirically found that the FCN value of an efficiency related value as determined above can be advantageously adjusted to provide an even more reproducible quantification value. For example, FIG. 12 is a plot of two sets of reaction data that illustrate how reaction curves for samples having the same initial concentration can vary due to different reaction anomalies. This figure illustrates two responses for samples containing equal quantities of an HIV target nucleic acid. However, in one response, the signal obtained from the reaction falls off early due to an anomaly in the reaction. This fall off can cause a FCN value determined from the maximum of the shifted ratio curve to vary substantially between the two samples, as illustrated in FIG. 13. However, the figure also shows that the two gradient curves are more substantially similar at early time or cycle number, which is plotted on the x-axis of the graph.

Thus, the invention involves determining an offset from the cycle number of maximum efficiency value (herein referred to as an FCN2 value), which is the location of another point on a reaction curve that can be used for analysis as described herein. In further embodiments, an Efficiency Related Value Threshold (ERVT) or Ratio Threshold (RT) value can be selected and used to determine a cycle number region of interest. An ERVT or RT can be an automatically or empirically determined value for a particular assay. The RT value can be set near to or at a criteria data level that is determined at the latter cycles during assay calibration.

One embodiment of a method of this invention starts at the FCN value on the shifted ratio curve and determines an earlier reaction point where the curve crosses the RT value. This reaction point is reported as an FCN2 value. It is believed that the FCN2 value provides improved linearity in samples having low copy numbers, in contrast with FCN values for certain assays, such as reactions where non-specific product formation reduces the efficiency of product formation in samples having low copy numbers.

FIG. 13 illustrates the desirability of using an offset efficiency value. This figure shows the shifted ratio curves for the responses shown in FIG. 12 and an RT line at 0.03. For this example, the FCN and FCN2 values are shown in Table 1.

TABLE 1

| Response | FCN | FCN2 | MR |
| --- | --- | --- | --- |
| Well 41 | 28.81 | 22.85 | 0.129 |
| Well 42 | 28.06 | 22.92 | 0.097 |
| Difference | 0.75 | 0.07 | 0.032 |

In this example, the curve of one response flattens out early and differs in shape from the curve of the other response, and the shifted ratio curve shows a difference. The early flattening can cause the earlier peak. In this example, the FCN2 values are more closely matched than the FCN values. In general, FCN and FCN2 values have been found to be more precise (lower standard deviations) than $C_t$ values. While these examples focus on use of the MR, it will be appreciated that other measures of the efficiency of the amplification reaction can be employed in the FCN and FCN2 embodiments of the present invention. Other efficiency related transforms useful in the context of the present invention include, but are not limited to, (a) use of first derivative, (b) use of the differences between sequential periodic data points, and (c) use of the slope or gradient of the log of the growth curve.

EXAMPLE 12

Quantification Using MR-FCN Analysis

Quantification is often desired in various types of reaction analysis. In PCR reactions, for example, quantification generally refers to an analysis of a reaction to estimate a starting amount or concentration of a target having an unknown concentration. The invention involves methods or systems or both for using an efficiency related value and a cycle number value (e.g., FCN) to perform a quantification. Specifically, the ERV of a test sample is compared to one or more of the ERV of at least one calibrator, preferably at least two calibrators, and, optionally, 3, 4, 5, or 6 calibrators, each of which contains a known quantity of a target nucleic acid.

In further embodiments, quantification can generally be understood as involving one or more calibration data captures and one or more quantification data captures. The calibration data and quantification are related using a quantification relationship or equation.

In calibration, a relationship between captured data, or a value derived from captured data (such as an FCN, FCN2, or MR, or combination of the foregoing), and one or more known starting concentration reactions is used to establish one or more parameters for a quantification equation. These parameters can then be used to determine the starting concentrations of one or more unknown reactions.

Various methods and techniques are known in the art for performing quantification and/or calibration in reaction analysis. For example, in diagnostic PCR settings, it is not uncommon to analyze test samples in a 96-well reaction plate. In each 96-well reaction plate, some wells are dedicated to calibration reactions with samples having known initial concentrations of target. The calibration values determined for these samples can then be used to quantify the samples of unknown concentration in the well.

Two general types of calibration methods are referred to as one-point calibration and standard curve (e.g., multiple points) calibration. Examples of these types are set forth below. Any suitable calibration method, however, can be used in the context of the present invention.

When there is no inhibition or interference, the PCR reaction proceeds with the target sequence showing exponential growth, so that after N cycles of replication, the initial target concentration has been amplified according to the relationship:

$$\text{Conc}_N \propto \text{Conc}_0 (1+e)^N$$

which can also be expressed as:

$$\text{Conc}_0 \propto \text{Conc}_N \times \frac{1}{(1+e)^N}$$

where $\text{Conc}_N$ represents the concentration of amplified target after N reaction cycles, $\text{Conc}_0$ represents the initial target concentration before amplification, N represents the cycle number and e represents the efficiency of the target amplification.

Quantitative data analysis is used to analyze real time PCR reaction curves so as to determine $\text{Conc}_0$ to an acceptable degree of accuracy. Previous $C_t$ analysis methods attempt to determine a cycle number at a reaction point where the $\text{Conc}_N$ is the same for all reactions under analysis. The FCN value determined by the methods of the invention provides a good estimate for the cycle number N for an assay in which no significant inhibition or signal degradation over the dynamic range of input target concentrations is demonstrated. The following proportionality relationship between a starting concentration and FCN can be used:

$$\text{Conc}_0(\text{FCN}) \propto 1/(1+e)^{FCN}$$

where $\text{Conc}_0(\text{FCN})$ represents the estimate of the initial target concentration determined by using the FCN value as determined by the methods of this invention.

In other words, the lower the starting concentration of target, the higher the FCN value determined for the PCR reaction. This relationship can be used for both calibration data and for quantification data.

This proportionality relationship can also be expressed as an equivalence, such as $$\text{Conc}_0(\text{FCN}) = K \times 1/(1+e)^{FCN}$$

where K represents a calibration proportionality constant.

For calibration data, $\text{Conc}_0(\text{FCN})$ represents a known concentration, such as 500,000 copies of target nucleic acid/mL; the exponent FCN is a FCN cycle number determined as described above; and e represents the efficiency value for a reaction, with e=1 indicating a doubling each cycle. These factors combine to form a relationship to allow for determination of the proportionality constant. Determination of the proportionality constant can only be made if there is a priori knowledge of the efficiency, e, of the amplification reaction. This a priori knowledge enables a one-point calibration. For quantification data, FCN values are determined for reactions involving samples having unknown concentrations of target. The FCN values are then converted to concentration values by use of the above equation. If the efficiency, e, is not known a priori, then a standard curve quantification method can be used. In this case, for calibration data, different samples having different levels of known concentration are amplified, and the FCN values of the samples are determined. These FCN values can be plotted against the log (base 10) of the known concentrations to describe a log (concentration) vs. FCN response. For an assay that demonstrates no significant inhibition or signal degradation over the dynamic range of input target concentrations, this response is typically well-fitted by a linear curve. The following equation describes the form of this standard curve:

$$\text{Log}_{10}(\text{Conc}_0(\text{FCN})) = m \times \text{FCN} + b$$

where $\text{Log}_{10}(\text{Conc}_0(\text{FCN}))$ represents the log (base 10) of the initial target concentration, m represents the slope of the linear standard curve, and b represents the intercept of the linear standard curve.

By using two or more known concentration calibration samples, a linear regression can be applied to determine the slope, m, and intercept, b, of the standard curve. For quantification data, FCN values are determined for reactions involving test samples of unknown concentration, which values are then converted to log (concentration) values by use of the above linear equation. Results can be reported in either log (concentration) or concentration units by the appropriate conversion.

It should be noted that the one-point calibration equation is easily converted to this linear standard curve form:

$$\text{Conc}_0(\text{FCN}) = K \times 1/(1+e)^{FCN}$$

$\text{Log}_{10}(\text{Conc}_0(\text{FCN})) = -\text{log}_{10}(1+e) \times \text{FCN} + \text{log}_{10}(K)$. The linear coefficient m can be used to calculate the efficiency of the particular PCR reaction.

EXAMPLE 13

Quantification Adjustments

When PCR reactions are subjected to inhibition, the resulting real-time PCR signal intensity can be depressed or delayed. The effect of this signal degradation on an efficiency related value such as MR is a reduction in that value. In addition, the effect of signal degradation on the fractional cycle number is generally to identify the FCN at an earlier cycle number than would be expected for the uninhibited reaction. These factors cause the plot of log (concentration) as a function of FCN to be less well described by a linear curve fitting function. Although higher order curve fitting functions can be applied for a standard curve, a linear fit requires fewer calibration levels and is simpler to calculate.

Some of these problems can be addressed in a standard curve analysis by incorporating an ERV or Intensity value into the quantification relationships as discussed above. Thus, the equations above can be rewritten a:

$$\text{Conc}_0(\text{FCN}_{Intensity\ Adj}) \propto \text{Intensity}/(1+e)^{FCN}$$

$$\text{Conc}_0(\text{FCN}_{MR\ Adj}) \propto \text{MR}/(1+e)^{FCN}$$

where Intensity represents the response intensity (above background) at the determined FCN value, MR represents the MR value as described previously. $\text{Conc}_0(\text{FCN}_{Intensity\ Adj})$ represents the estimate of the initial concentration of the target determined by using the FCN value adjusted by using the Intensity value and $\text{Conc}_0(\text{FCN}_{MR\ Adj})$ represents the estimate of the initial concentration of the target determined by using the FCN value adjusted by using the MR value.

These expressions take advantage of the relationship observed between the intensity at the selected FCN cycle or the MR determined at the selected FCN cycle, or both, and the change to the FCN value in the presence of inhibition, as discussed above. The net effect is that the right hand side of the proportionality expressions above is relatively insensitive to inhibition and other factors that affect the PCR amplification curve, and, therefore, provide significant robustness as expressions for determining the concentration values of the target.

The following discussion further explains the properties and relationships of FCN, $FCN_{Intensity\ Adj}$, and $FCN_{MR\ Adj}$. Assuming the efficiency is 1, the previous can be simplified to:

$Conc_0(FCN) \propto 1/2^{FCN}$ $Conc_0(FCN_{Intensity\ Adj}) \propto Intensity/2^{FCN}$ $Conc_0(FCN_{MR\ Adj}) \propto MR/2^{FCN}$ Taking the Log base two of the expressions yields:

$Log_2(Conc_0(FCN)) \propto FCN$ $Log_2(Conc_0(FCN_{Intensity\ Adj})) \propto FCN - Log_2(Intensity)$ $Log_2(Conc_0(FCN_{MR\ Adj})) \propto FCN - Log_2(MR)$ From the right sides of the expressions come the values for compensating for intensity or MR to adjust the FCN value by means of the following formulas:

$FCN_{Int.\ Adj.} = FCN - Log_2(Intensity)$ $FCN_{MR.\ Adj.} = FCN - Log_2(MR)$.

This calculation then provides quantification by using adjusted FCN values analogous to using FCN values or $C_t$ values. It should be noted that the use of these adjusted FCN values provide significant robustness to inhibition and other factors that affect PCR amplification, such as $C_t$ values used in determining the concentrations of the target in the unknown samples. The plot of Log (concentration) vs. these adjusted FCN values is generally well fitted by a linear standard curve. Thus, the present invention provides a method for determining the quantity of a target nucleic acid in a sample comprising involving the steps of (a) finding the period of time or cycle number of an amplification reaction corresponding to a maximum of an efficiency related value, preferably of an MR, and (b) adjusting that value by subtracting a logarithm of the Intensity or a logarithm of the MR, and (c) comparing the value obtained to calibration data obtained using the same methodology.

EXAMPLE 14

Standard Curve Calibration

Figure 14:
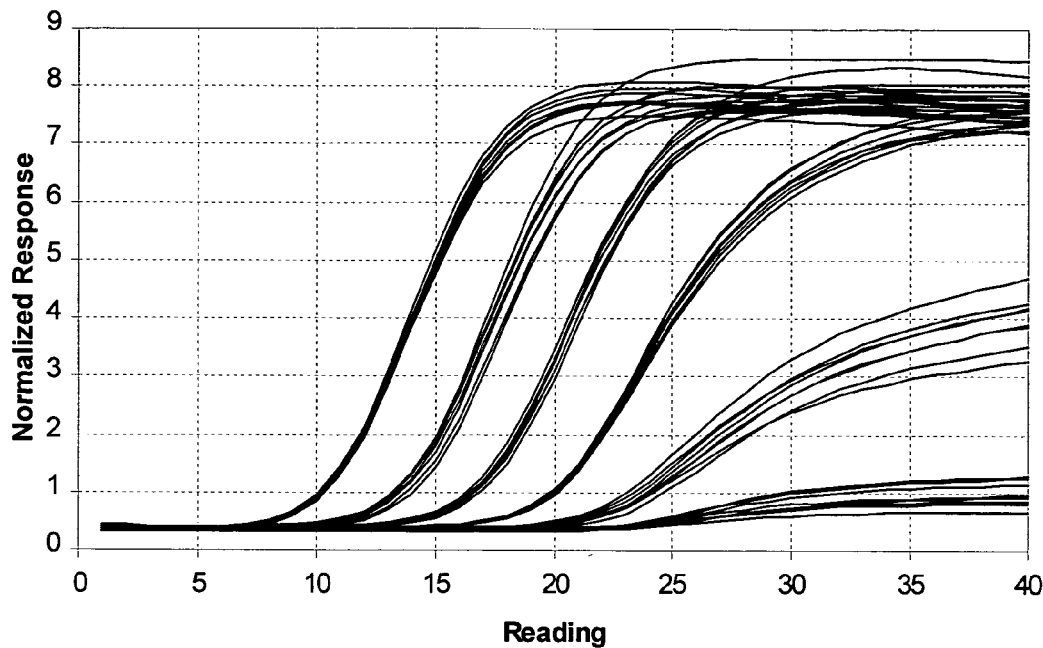
FIG. 14 illustrates data for an HIV assay run with eight replicates of known concentration samples at 50, 500, 5,000, 50,000, 500,000 and 5,000,000 copies per mL.

Development of a standard curve from known concentrations and use thereof for quantification is well known in the art and can be further understood from the following example. In a typical case, a number of calibration reactions (such as in wells in which the initial concentrations are known) are used during each amplification or series of amplifications to perform the calibration operation. One problem that arises with attempting to quantify a target nucleic acid in a sample through a large range of possible initial concentrations is that quantification of lower quantities of target nucleic acid in any particular reaction becomes more difficult. For example, FIG. 14 illustrates data for an assay designed to quantify the amount of HIV in test samples. The reactions were performed with eight replicates of six known concentrations of target nucleic acid, which were 50; 500; 5,000; 50,000; 500,000; and 5,000,000 copies per mL. The assay data show significant signal suppression in reactions where the copy number is low (the curves farthest to the right). While quantity of the four highest concentrations of target nucleic acid (the curve sets to the left) yielded precise results with low coefficients of variability, the two lowest concentrations produced less precise curves. The imprecision caused by the difficulties in quantifying low concentrations of target nucleic acids in assays having a dynamic range of 100,000 to 1 or more can be addressed by the following methods of this invention.

Because calibration runs in a reaction plate are relatively expensive, it is conventional to collect a minimal acceptable number of calibration data sets. For example, in one implementation, the average of two replicates each of the 500; 50,000; and 5,000,000 copy/mL samples are run along with the diagnostic assays, thereby requiring perhaps six wells in a 96 well plate to be used for calibration reactions.

Figure 15:
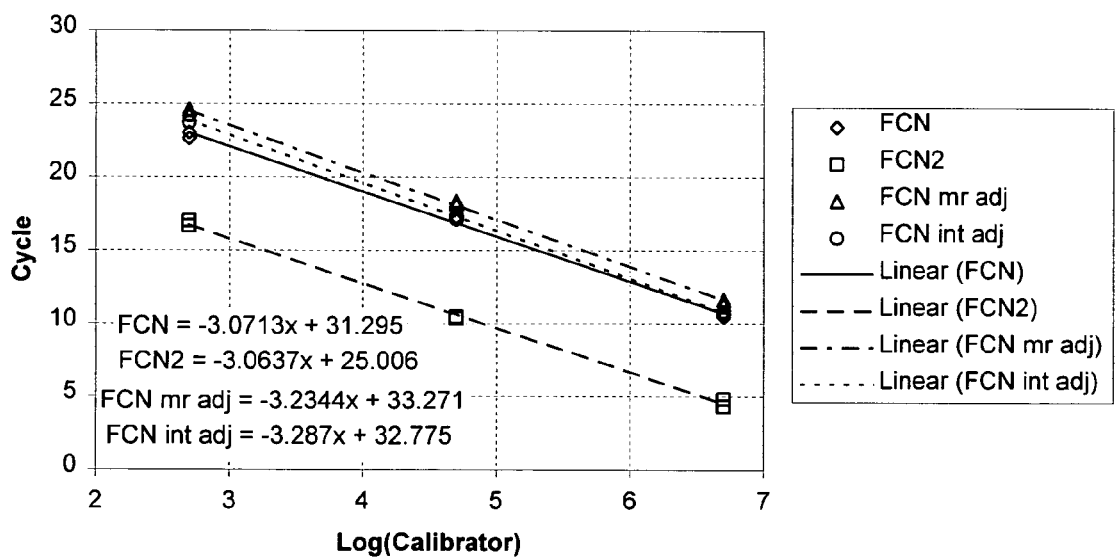
FIG. 15 is a plot illustrating four linear standard curves generated from three-point calibration data using four different cycle number related values (e.g., FCN, FCN2, $FCN_{MR\ Adj.}$, and $FCN_{Int.\ Adj.}$) according to embodiments of this invention.

Because the relationship between the cycle numbers and the log of the calibrator concentration is substantially linear, a linear regression can be performed between a log (e.g., $log_{10}$) of the calibrator concentrations and the cycle number. This regression can easily be performed via the Excel program and other mathematical analysis software. FIG. 15 illustrates four linear standard curves generated from three-point calibration data using four different cycle number related values (e.g., FCN, FCN2, $FCN_{MR\ Adj.}$, and $FCN_{Int.\ Adj.}$).

In each of the curve fit equations, the x-axis displays values of the $Log_{10}$ [Target] actual or known concentration. Thus, solving for x provides an expression for converting from cycle number related values to $Log_{10}$ (Target) calculated concentration of the assay. If the assay response is not linear with Log (Target), a higher order or more complex regression, or a larger number of calibration reactions, or both, can be used. In this example, the following equations were determined:

$FCN = -3.0713 * Log_{10}(Conc_0) + 31.295$ $FCN2 = -3.0637 * Log_{10}(Conc_0) + 25.006$ $FCN_{MR\ adj} = -3.2344 * Log_{10}(Conc_0) + 33.271$ $FCN_{Int.\ adj} = -3.2870 * Log_{10}(Conc_0) + 32.775$

EXAMPLE 15

Comparing Quantification Using Different Cycle Number Related Values

Figure 16:
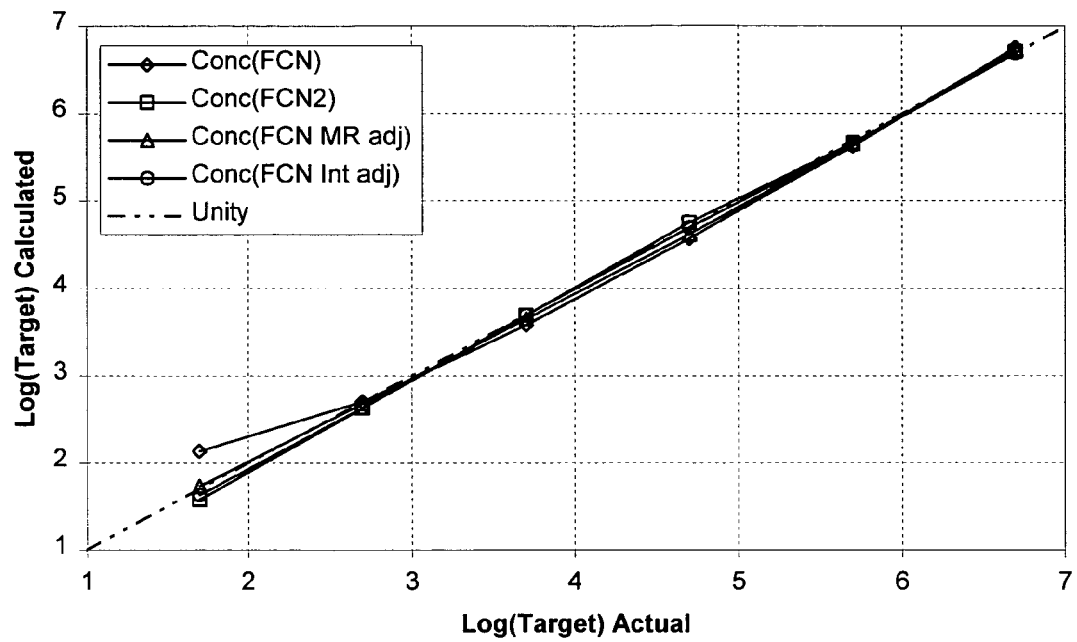
FIG. 16 compares calculated concentrations to known concentrations for the data illustrated in FIG. 14 using the four curves illustrated in FIG. 15 according to embodiments of this invention.

In order to examine the different characteristics of calibrations using the different cycle number related values described above, quantification can be performed on various samples having known concentrations, and the concentrations calculated compared with the known concentrations. In one example of such a comparison, the standard curves having the parameters generated above were used to carry out quantification of the assay responses shown in FIG. 14. The mean of the calculated concentrations of the eight replicates at each known concentration was compared to the known concentration value. FIG. 16 compares $log_{10}$ of the known concentration values (x-axis) to the means of the $log_{10}$ of each of the calculated concentrations for the eight samples at each concentration.

As indicated by FIG. 16, the 50 copies/mL samples (log (concentration)=1.7) are slightly over-quantified (i.e., higher than the actual concentration) using FCN, while the accuracy for the FCN method (of the MR) at the higher concentrations is very good. FCN2 is more accurate at the lowest concentration, but somewhat under-quantified (i.e., lower than the actual concentration), and exhibit less linearity and accuracy at some higher concentrations. $FCN_{MR\ Adj.}$ showed very accurate and linear quantification throughout the concentration range. $FCN_{Int.\ Adj.}$ also showed substantial improvement in accuracy and linearity compared to FCN, except for very slight under-quantification at the lowest concentration. Accordingly, all four methods work well, but some are better than others for particular situations. Therefore, the skilled artisan can easily select an appropriate method for any particular application to obtain excellent results.

EXAMPLE 16

Quantification Using One-Point Calibration

A one-point calibration can be used for quantification. In this case, two wells at the 50,000 copies/mL concentration (Log (4.7)) were used for calibration. In order to calculate the calibration constant, the following equation is used: $K=Conc_0 * 2^{FCN}$, where K represents the calibration constant, $Conc_0$ represents the known concentration of the calibrator, FCN represents the fractional cycle number of the calibrator, and the efficiency of the reaction, e, as described earlier, is assumed to be 1. Similar calibration constants can be generated using the proportionality relationships such as FCN2, $FCN_{MR\ Adj.}$ and $FCN_{Int.\ Adj.}$.

Figure 17:
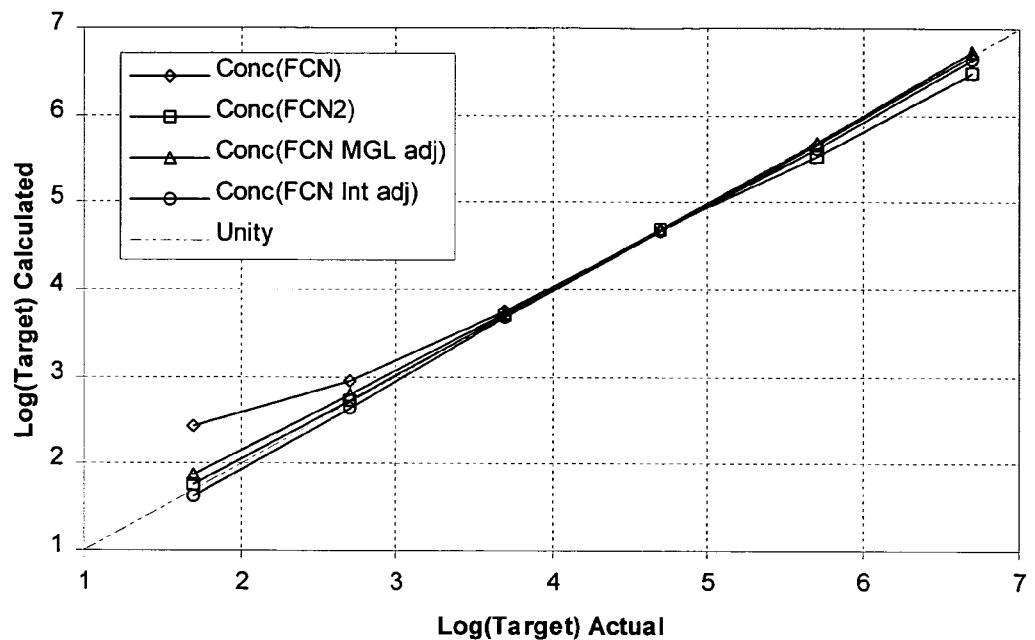
FIG. 17 illustrates results using a one-point calibration according to embodiments of this invention.
Figure 18:
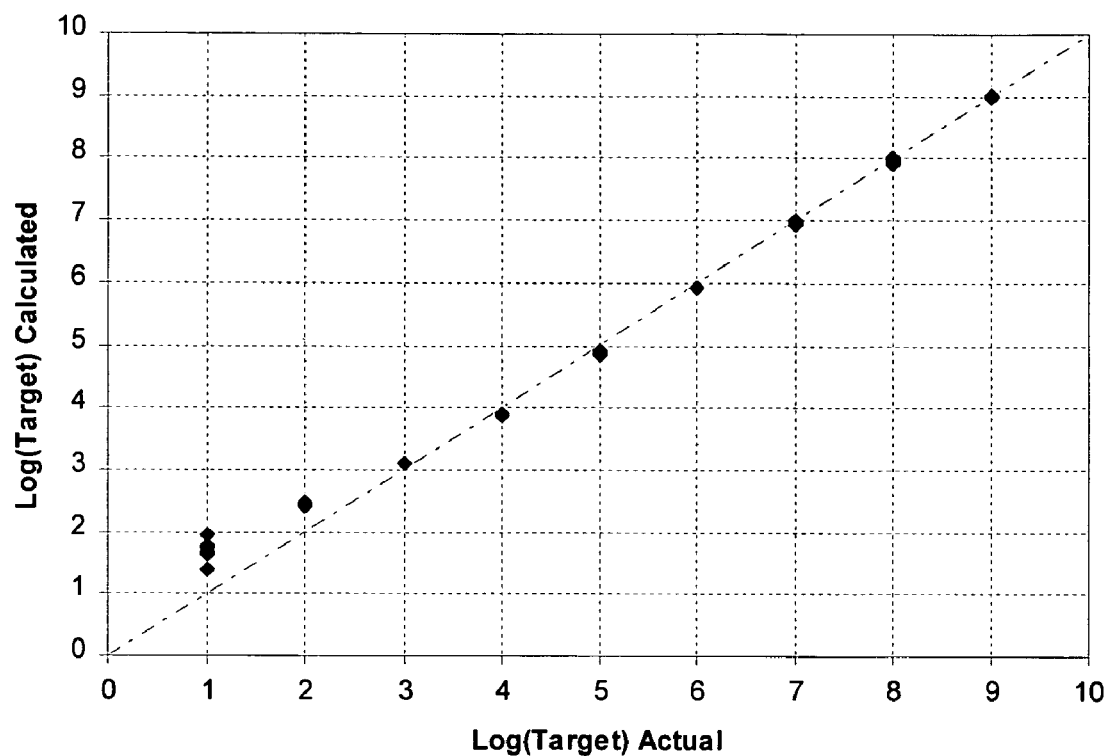
FIG. 18 illustrates experimental HBV results using MR analysis with a one-point calibration according to embodiments of this invention.

In this case, the constant was generated for two wells and the average was used. Once the calibration constant is generated, the concentration for each assay is calculated with the following equation: $Conc=K_{FCN}/2^{FCN}$. FIG. 17 illustrates resulting from a one-point calibration.

As can be seen, the FCN results are elevated at the lowest two concentrations and accurate from log (Conc) equals 3.7 and above. FCN2 shows improved accuracy at low concentrations compared to FCN, but under-quantifies at log (Target) equal to 5.7 and 6.7. FCN-MR adjusted shows good linearity over the entire range with slight over-quantification at the two lowest concentrations. FCN-Intensity adjusted also shows good linearity with very slight under-quantification at the lowest two concentrations. Accordingly, each of these embodiments works well and the skilled artisan can readily select from among these options.

As discussed above, an FCN-MR analysis can be used to characterize a particular reaction as positive or negative or to compare the reaction to criteria data, or both. These values can be used to quantify a reaction. A variety of quantification methods can benefit from FCN-MR analysis rather than $C_t$ analysis.

In one embodiment, a FCN value, a FCN2 value, or a FCN adjusted value can be used in any way that a $C_t$ value has been used in the prior art. Typically, but not necessarily, FCN-adjusted, FCN2-adjusted, or FCN-adjusted analysis can be applied to various sets of calibration data to thereby develop reference data curves or an equation for comparing the result of a reaction in which the concentration of target is unknown to the results of reactions in which the concentration of target is known. Thus, the present invention can be used to develop reference data and to perform a comparison wherein two values (e.g., FCN-MR) are used both for developing reference data and also for making a comparison to that data.

While experiments using the MR method regularly used different preprocessing steps on the captured data set before processing the data set with a ratio function, most of these steps are not required. In particular, experimental results have indicated that scaling, normalization by a reference dye, baselining (both offset and slope correction), and filtering are not required. However, filtering has generally been found to be desirable as it improves performance in the presence of noise. Slope correction (for the baseline region) has also been found to be desirable as it slightly improves discrimination between samples that do not contain target nucleic acid and those that contain very little target nucleic acid or suffer from significant inhibition of the amplification reaction. Generally, however, when $FCN_{Intensity\ adj}$ is used, it is preferable to use a normalization technique, such as, but not limited to, scaling or normalization to a reference dye.

EXAMPLE 17

MR Algorithm Applied to HBV Data Using a One-Point Calibration

HBV assays of control solutions ranging from 10 copies/reaction to $10^9$ copies/reaction and negatives were processed on an ABI Prism 7000 with six replicates at each concentration. The captured data was processed using only a digital filter. FCN values were then calculated using a MR algorithm as described above. The concentrations were calculated by means of a one-point calibration using the three of the responses at $10^9$ copies/reaction as a reference calibrator.

Even without normalization, scaling, or baselining, the resulting quantification was very good, with the exception of an acceptable amount of over-quantification of the 10 copies/reaction and 100 copies/reaction samples (i.e., the Log (Target)=1 and 2 samples). There was a very clear distinction between the negatives and the 10 copies/reaction assays, with no false positives or false negatives. Additional results indicated that when the same data was quantified with $C_t$ analysis, the 10 copies/reaction and 100 copies/reaction assays are also slightly over-quantified, and the precision at all concentrations above 10 copies/reaction is better with the MR analysis. In this case, the $C_t$ results were normalized, baselined, and calibrated by means of a two-point calibration with three replicates each at concentrations $10^3$ and $10^7$ copies/reaction.

Figure 19:
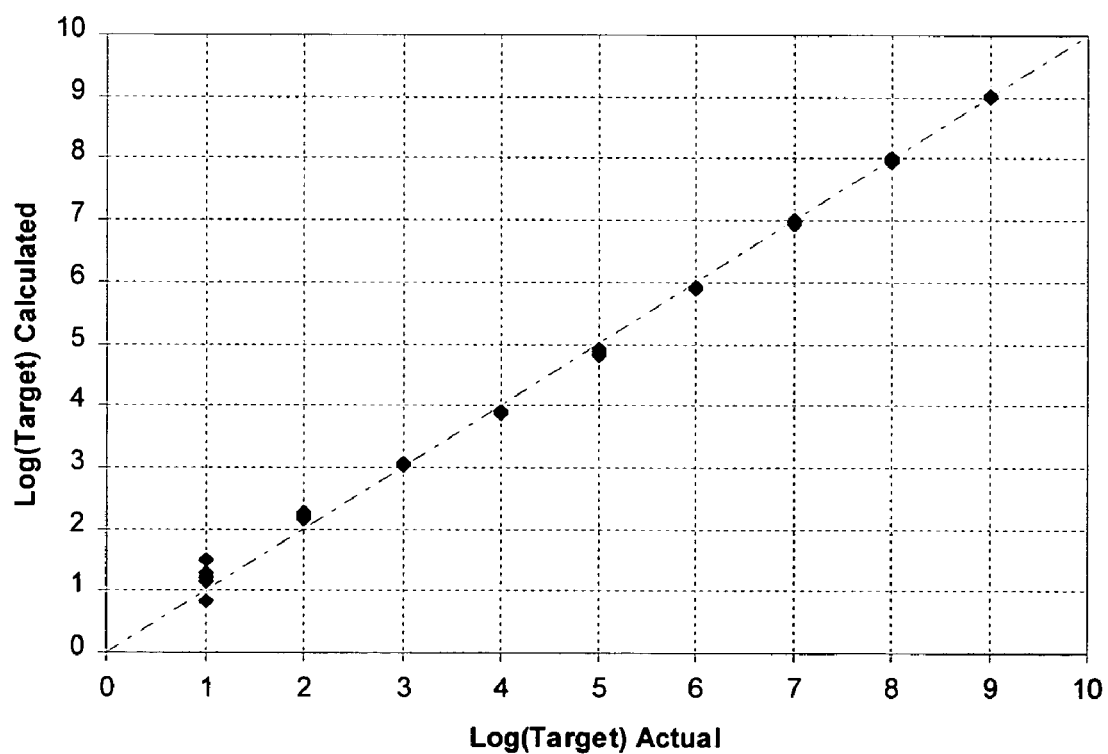
FIG. 19 illustrates experimental HBV results using MR analysis and $FCN_{MR\ adj.}$ with a one-point calibration according to embodiments of this invention.
Figure 20:
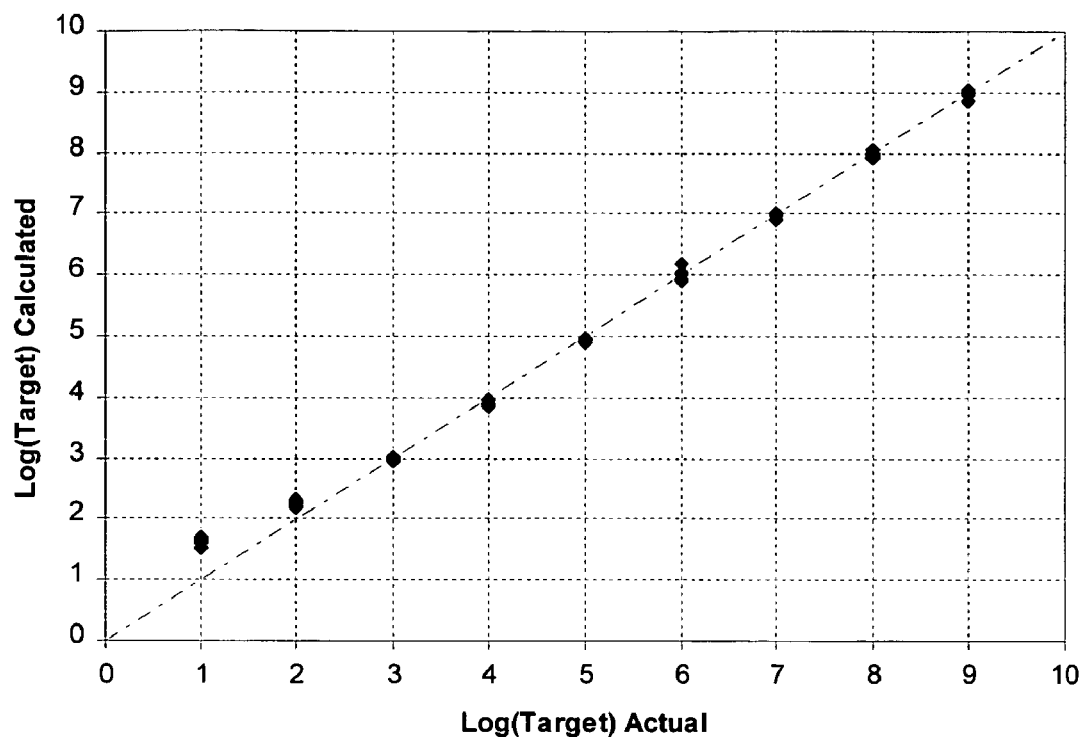
FIG. 20 illustrates experimental HBV results using $C_t$ analysis and a one-point calibration according to embodiments of this invention.

FIG. 19 illustrates an example of the same HBV data using MR analysis and with $FCN_{MR\ adj.}$, correction. Again, the quantification was performed by means of a one-point calibration with three responses at the $10^9$ copies/reaction with no normalization, scaling, or baselining. As can be seen, the over-quantification of the low concentrations is significantly reduced, i.e., the quantitative results are significantly improved.

EXAMPLE 18

MR Algorithm Applied to HIV Data

Figure 21:
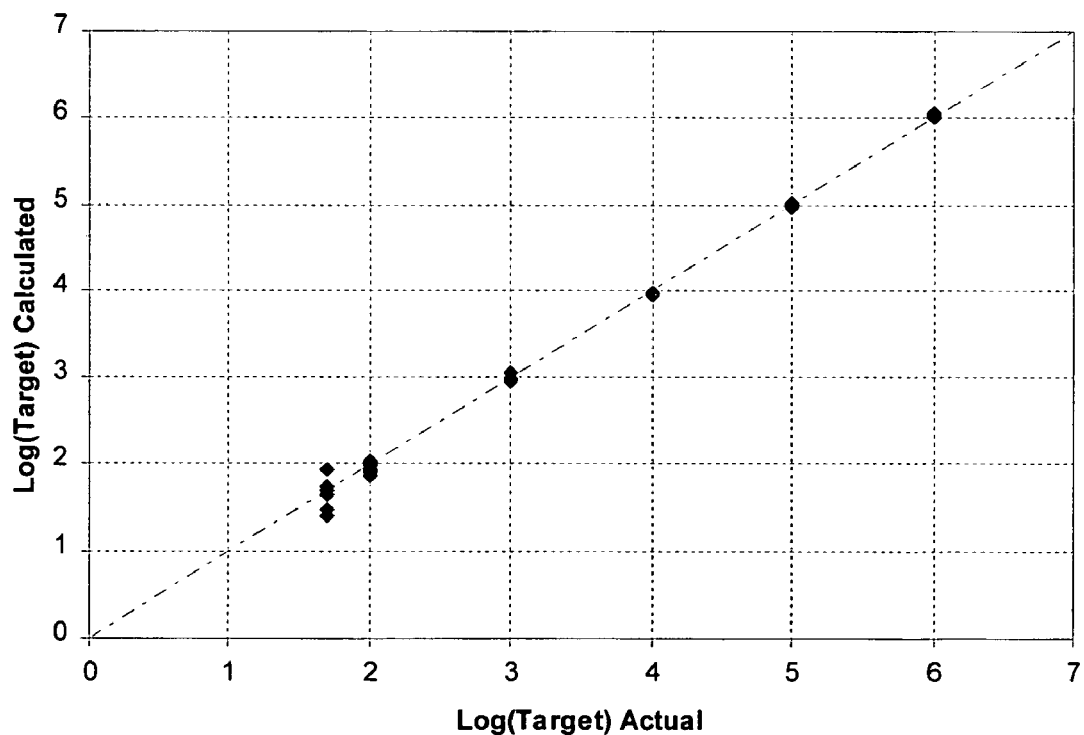
FIG. 21 illustrates experimental HIV results using MR analysis and one-point calibration, e.g. using $10^3$ and $10^7$ copies/mL responses as calibrators, according to embodiments of this invention.

In this example, HIV assays of control solution were performed at concentrations of negatives, 50 copies/mL, and 100 copies/mL, through $10^6$ copies/mL in replicates of six. The responses were processed by means of the MR algorithm using $FCN_{MR\ Adj.}$ with normalizing and baselining. FIG. 21 illustrates results the example using MR analysis and two-point calibration, e.g., using two replicates of the $10^2$ and $10^5$ copies/mL responses as calibrators. There was clear differentiation between the negatives and the 50 copies/mL assays with no false positives or false negatives. As can be seen, there is good linearity and precision.

EXAMPLE 19

Validity Determination Using Target and IC (FCN, MR) Pairs

It has been found that pairs of reaction time or cycle number values and efficiency related values (e.g., pairs of FCN- MR values) can provide valuable information about a nucleic acid amplification reaction, e.g., a PCR reaction, which can be further enhanced by considering data pairs for both the internal control and target amplification reactions. While pairs for a target reaction alone carry important information about reaction efficiency and can be used for comparison with criteria data, additional factors that arise in processing samples or in the samples themselves may be better analyzed by considering control data as well.

For example, in processing specimens for use in PCR or other suitable amplification reactions, the sample can carry various inhibitors into the reaction, which might be detectable through assessment of target data only. However, abnormal recovery of target nucleic acid during sample preparation typically would not be detected by analysis of a single amplification reaction. Furthermore, a target nucleic acid may possess polymorphic sequences that could impair detection of the target nucleic acid, e.g., if a probe is used that binds to a polymorphic region of the sequence. Mismatches caused by the polymorphic sequence in this region would affect the detected signal, and, consequently, the amplification might not appear as abnormal or inhibited using the evaluation of data pairs for a single amplification. Co-analysis of an internal control together with analysis of the target amplification responses can provide accurate quantification of the target nucleic acid in such samples when other methods would typically indicate an invalid reaction.

Thus, pairs of reaction time or cycle number values and efficiency related values can be used together to assess the validity of a given reaction, such as in a given container or well. One could design the internal control (IC) amplification reaction to be comparable in robustness to the target amplification reaction, or slightly less robust. Robustness in this context means the sensitivity of the reaction performance to factors that can affect the PCR processing pathway, such as inhibition that results from sample preparation or the samples themselves, or to variability in transferring of the reaction mixture by pipette, such as transferring inaccurate amounts of amplification reagents by pipette.

EXAMPLE 20

Multiple Criteria Data Curves

Figure 22:
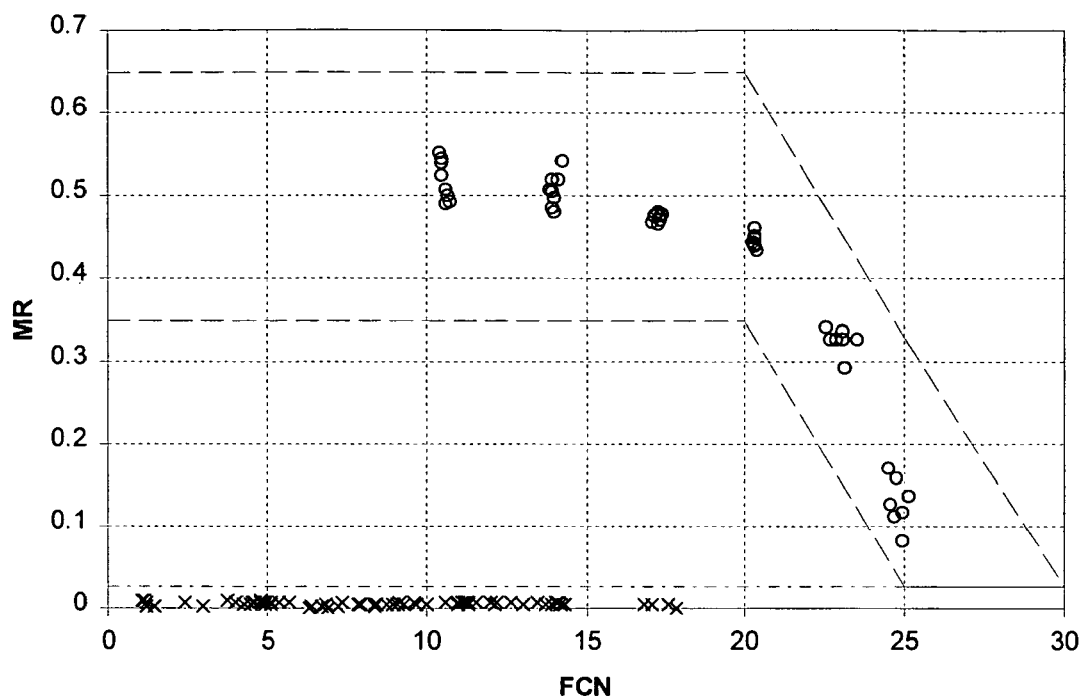
FIG. 22 is a plot illustrating two types of criteria data according to embodiments of this invention wherein the lower horizontal line represents criteria data suitable for differentiating negative reactions from positive reactions.

Multiple criteria curves for the pairs of cycle number value—efficiency related value (e.g., FCN-MR pairs) can be developed and can have different uses or levels of importance, particular for use with validity determination. For example, a first criterion curve can be selected so as to be able to discriminate reactive amplification signals from non-reactive responses. A second criterion curve can be selected so as to be more constraining than the first type, so that it would be useful in identifying sample responses that lead to accurate quantification in contrast to those having partial inhibition that might have lower confidence in quantification. FIG. 22 is a plot illustrating two types of criteria data, wherein the lower horizontal line represents criteria data suitable for differentiating negative from reactive reactions. The second set of lines represents criteria data indicating the normal range for the FON-MR pair responses. These criteria can be used to distinguish high confidence in quantification in contrast to a lower confidence that might be associated with a value outside this range due to partial reaction inhibition.

For example, the first type of criteria data that differentiates reactive and non-reactive amplification reaction can be referred to as "MR criteria data." These data act as a cutoff threshold reactive responses will have MR values that exceed the MR criteria data, whereas negative samples will have MR values that will not exceed the criterion value or criterion line. The criteria data is preferably set so that noise in the response signal does not exceed the criteria, nor will such biases as cross-talk or bleed-over.

The second type of criteria data is referred to as the MR normal range. This range would be the range of MR values for a given FCN over which quantification of the sample is accurate. If a signal response is suppressed, the MR value observed will drop. As the MR value decreases due to inhibition, the FCN value can shift to earlier cycles, whereas a threshold based $C_t$ might shift to later cycles. The MR normal range would be the range for MR values in a criteria data set for which a chosen value related to a cycle number would provide an accurate quantitative result for the sample when used to determine the concentration of target in the sample from the assay standard curve.

Figure 23:
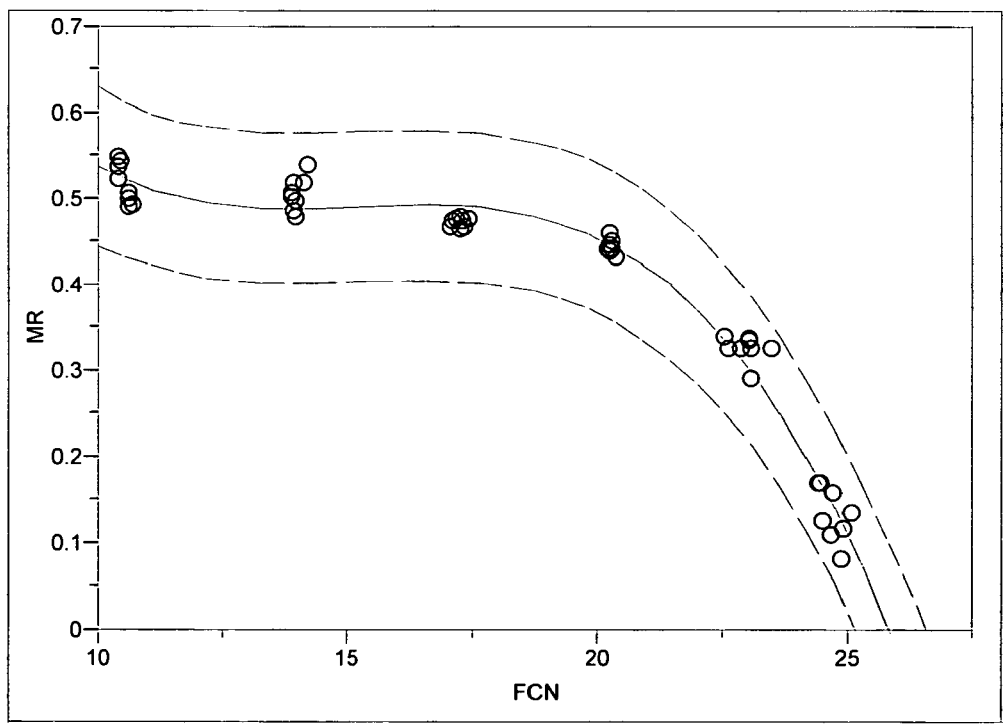
FIG. 23 is a plot illustrating FCN-MR for HIV data from 50 copies/mL to 5,000,000 copies/mL analyzed by a statistics software package to apply a curve fit to the data and to determine confidence intervals according to embodiments of this invention.

The "MR normal range" can be developed using a Bivariate Fit of the MR by FCN as will be understood in the art. FIG. 23, for example, shows a FCN-MR plot for HIV data from 50 copies/mL to 5,000,000 copies/mL. The data was analyzed by means of a statistics software package (such as JMP (SAS Institute, Inc.)) to apply a cubic curve fit to the data. This cubic curve fit is represented by the solid line in middle of the figure. The upper and lower dashed curves represent the confidence interval generated using a confidence interval individual analysis option with an alpha level of 0.001. TABLES 2A, 2B, and 2C illustrate sample data input and output related to FIG. 23.

TABLE 2A

| Summary of Fit | |
| --- | --- |
| RSquare | 0.971668 |
| RSquare Adj | 0.969737 |
| Root Mean Square Error | 0.023918 |
| Mean of Response | 0.401317 |
| Observations (or Sum Wgts) | 48 |

Polynomial Fit Degree = 3
MR = 0.6710196 − 0.0101107 FCN−0.0039387 (FCN-18.3056)^2 − 0.0004202 (FCN-18.3056)^3

TABLE 2B

| Analysis of Variance | | | | |
| --- | --- | --- | --- | --- |
| Source | DF | Sum of Squares | Mean Square | F Ratio |
| Model | 3 | 0.86331003 | 0.287770 | 503.0120 |
| Error | 44 | 0.02517212 | 0.000572 | Prob > F |
| C. Total | 47 | 0.88848215 | | <.0001 |

TABLE 2C

| Parameter Estimates | | | | |
| --- | --- | --- | --- | --- |
| Term | Estimate | Std Error | t Ratio | Prob > \|t\| |
| Intercept | 0.6710196 | 0.036617 | 18.33 | <.0001 |
| FCN | −0.010111 | 0.002006 | −5.04 | <.0001 |
| (FCN-18.3056)^2 | −0.003939 | 0.000198 | −19.92 | <.0001 |
| (FCN-18.3056)^3 | −0.00042 | 0.000047 | −8.93 | <.0001 |

A statistically derived confidence interval, as shown, is a systematic approach to determining which data points represent "normal" responses and should therefore be quantified. Data points lying outside this interval are exceptional and are preferably identified to a human operator by a software program so that further investigation can be made.

In alternative embodiments, such a curve can be simplified in the form of one or more straight-line segments. This simplification can in some cases be performed by a technician viewing the raw data or may be derived from an alpha interval as discussed above.

Figure 24:
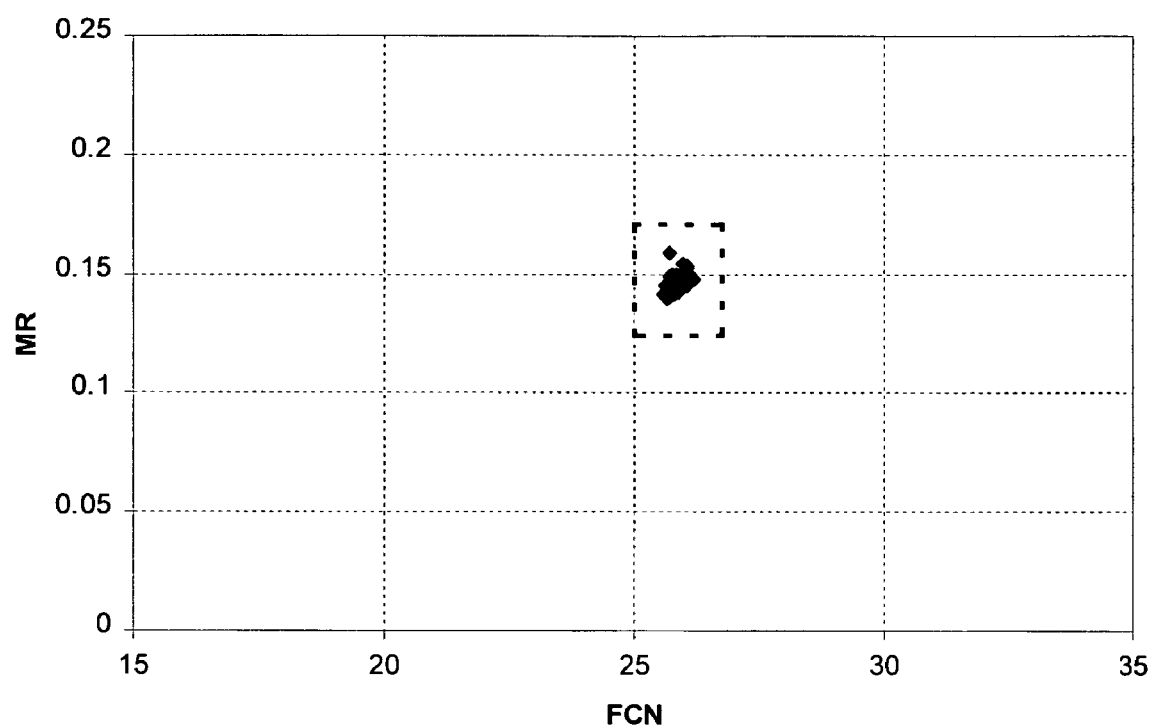
FIG. 24 is a plot illustrating internal control data analyzed by a statistics software package to determine confidence intervals according to embodiments of this invention.

A similar statistical fit can be performed on the internal control (IC) data. FIG. 24, for example, shows a plot of MR as a function of FCN for IC data, namely IC data associated with the data shown in FIG. 23. This data can be used to determine an IC criterion, which, for example, can be a single value that is five standard deviations below the mean of the MR values of the IC or can be a range or box of values, for example, based on the mean±5 standard deviations of the MR and FCN values.

Thus, the present invention also provides a method for analyzing an amplification reaction, the method comprising establishing a "confidence corridor", which is a range of selected values provided in pairs in which the first value is a maximum efficiency related value (which is preferably the MR), and the second value is a time value or cycle number value at a reaction point (which optionally can be fractional). The method further comprises determining whether a maximum efficiency value occurring at any particular periodic time value or cycle number value at a reaction point (which optionally can be fractional) falls within the selected range. If the value does not, then further investigation, or disregarding the results, is indicated. Any suitable method can be used to establish the selected confidence corridor. Preferred methods include setting the confidence corridor about 1, 2, 3, 5, 10, or any other suitable number of standard deviations from the mean of data obtained from a set of reactions used to characterize the assay. Another suitable method involves modifying the confidence corridor by observing known aberrant or discrepant results and modifying the confidence corridor to exclude a portion of those aberrant or discrepant results in future assays. The use of the confidence corridor of the present invention can be applied to target nucleic acid quantification, analysis of any of standards, calibrators, controls, or to combinations of the foregoing.

EXAMPLE 21

Validity Analysis

Figure 25:
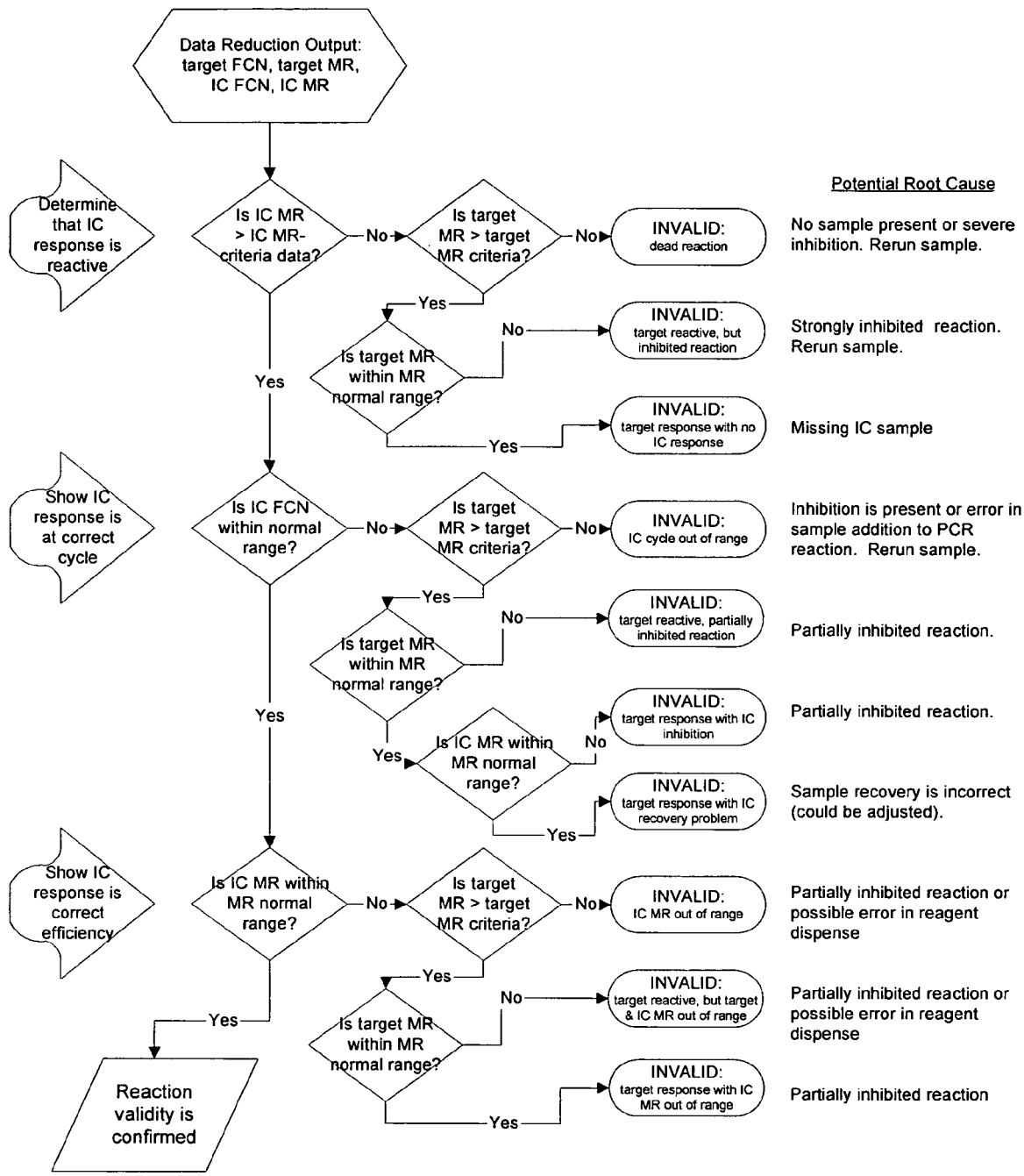
FIG. 25 is a flow chart illustrating a logic analysis tree for assessment of assay validity through analysis of pairs of cycle number related value—efficiency related value for both the internal control and the target amplification reactions according to embodiments of this invention.
Figure 26:
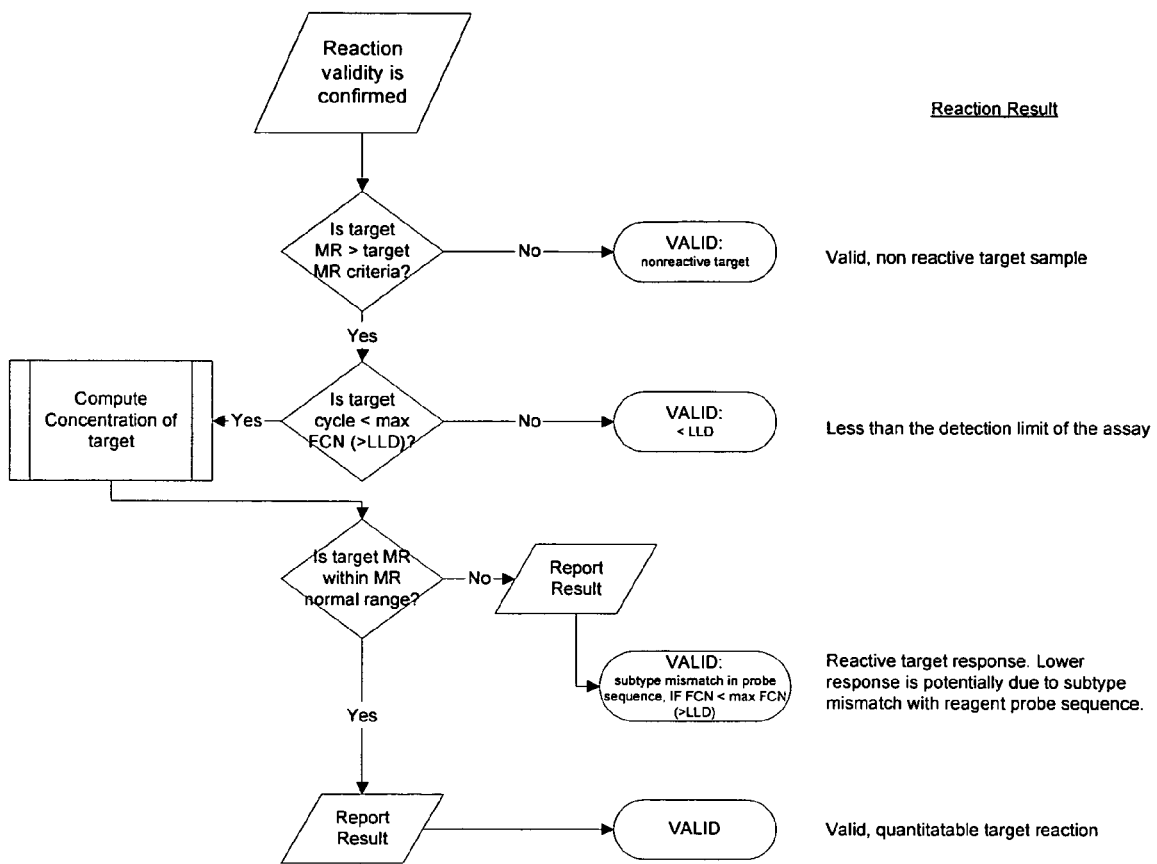
FIG. 26 is a flow chart illustrating a logic analysis tree for reporting target results with validity criteria assessment using the pairs of cycle number related value—efficiency related value according to embodiments of this invention.

FIG. 25 is a flow chart illustrating a logic analysis tree for assessment of assay validity through analysis of pairs of cycle number (e.g., FCN) minus of ERV (e.g., MR) for both the internal control and the target amplification reactions. FIG. 26 is a flow chart illustrating a logic analysis tree for reporting target results with validity criteria assessment using pairs of cycle number (e.g., FCN) minus ERV (e.g., MR). In the flow charts, FCN is used for clarity of illustration, but as noted elsewhere herein, other methods can be used to generate the reaction point value, for example, $C_t$ method, FCN2, $FCN_{MR\ Adj.}$ or $FCN_{Int.\ Adj.}$, or other suitable method.

Thus, a validity check can optionally proceed as a series of questions regarding the internal control (IC) and/or target data.

In FIG. 25, the left-most arrow blocks provide general descriptions of the steps of the method. Details of method(s) can be understood further by considering the following. The method analyzes a cycle number/ERV pair from both a target and control (IC) reaction. Initially, if (1) the IC MR is above the IC MR criteria data, and then if (2) the IC FCN is within the normal range, and further if (3) the IC MR is within the normal range, then reaction validity is confirmed.

As shown in the figure, an invalid result can be further characterized or explained by considering one or more characteristics of the target MR.

FIG. 26 illustrates a method for analyzing the target data for valid reactions to further characterize a valid result as indicating (1) a non-reactive target sample, (2) a target at a concentration of less than the detecting limit of the assay, (3) a target present but with a quantification inhibited, possibly due to sub-type mismatch, or (4) a valid, quantifiable target reaction.

Thus, by combining the analysis based on multiple targets and using both cycle number and efficiency related values, one can distinguish an inhibited sample from a sample that suffered from poor nucleic acid recovery during sample preparation. The analysis makes use of pre-established knowledge of the assay that is contained in the internal control and target criteria data.

EXAMPLE 22

Validity Determination Using Peak Width

In contrast to the conventional $C_t$ analyses in the prior art, which only presents a single value describing an amplification response, an efficiency related value analysis (and preferably an MR analysis) can provide an efficiency related transform curve with data corresponding to the time value or cycle number value of the entire amplification reaction or any portion thereof. It has been discovered that within a specific assay formulation, normal assay responses generate highly reproducible efficiency related transform curves. One characteristic in particular is the width of the peak of the efficiency related transform curve. It has been found that the width of the peak of the efficiency related transform, e.g., as defined by its width at the half maximum height, varies very little even when the magnitude of the fluorescence intensity varies greatly.

Figure 27:
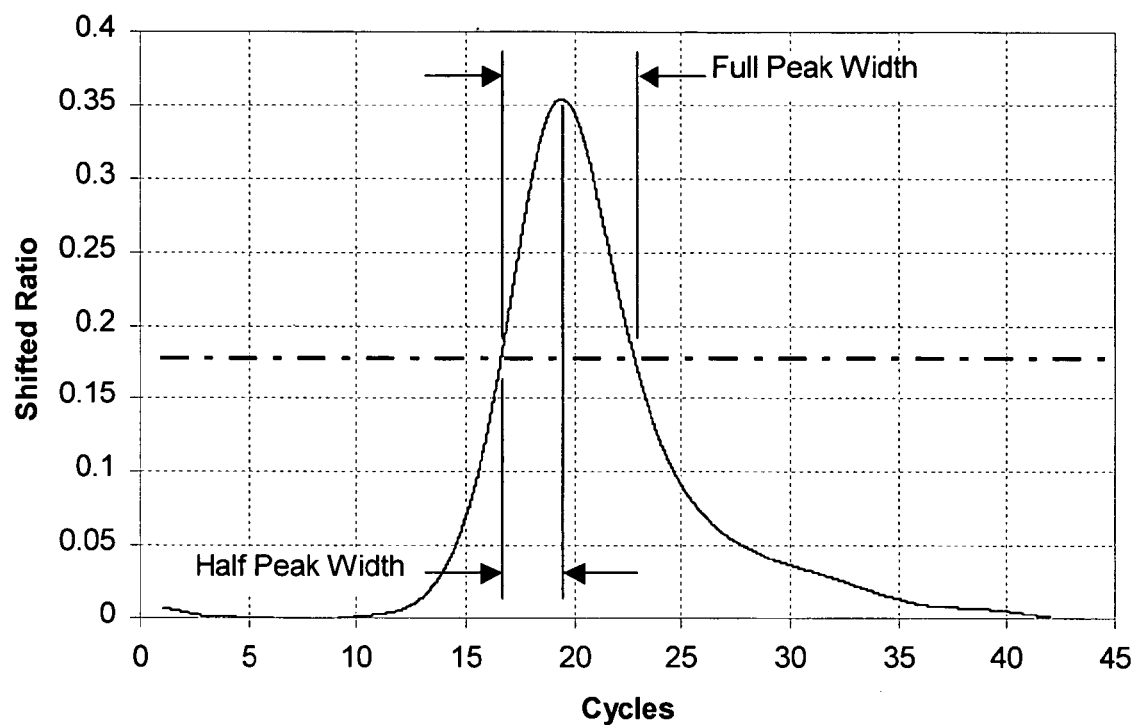
FIG. 27 illustrates the calculation of peak width measurements according to embodiments of this invention.
Figure 28:
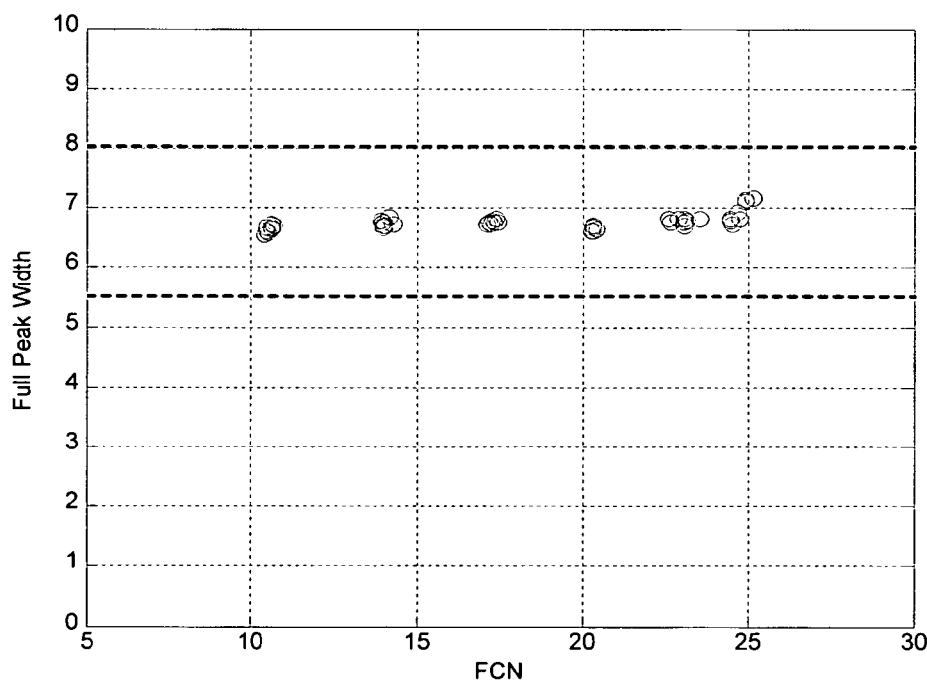
FIG. 28 illustrates experimental HIV results using the full peak width measurement according to embodiments of this invention.

Any suitable method can be used to determine the width of the peak of the efficiency related value. FIG. 27 depicts one suitable method for determining the width of an efficiency related value peak. In FIG. 27, the full peak width is the width in cycles of the peak at it half maximum level. The HIV responses in FIG. 14 show normalized fluorescence for samples of higher concentration at approximately 8, while the normalized fluorescence for the samples of low concentration is as low as about 1. Using the shifted ratio method to calculate an efficiency related transform for each amplification reaction and computing the full peak width provides the results shown in FIG. 28. Even with an eight-fold change in final fluorescence intensity, the peak widths are surprisingly conserved within a narrow range. Accordingly, the present invention provides amplification reaction validity criteria, wherein an amplification reaction is deemed valid when the width of the peak of an efficiency related value is contained within a selected range characteristic of the amplification reaction. In FIG. 28, the dashed horizontal lines in bold type represent the mean of the width measurements plus and minus 10 standard deviations. Width measurements that are not within the range of about 5.5 and 8.0 (as shown in FIG. 28) are considered invalid or at least suspect. The skilled artisan can readily vary the parameters describing the acceptance interval, depending on the requirements of the particular assay and without undue experimentation.

Figure 29:
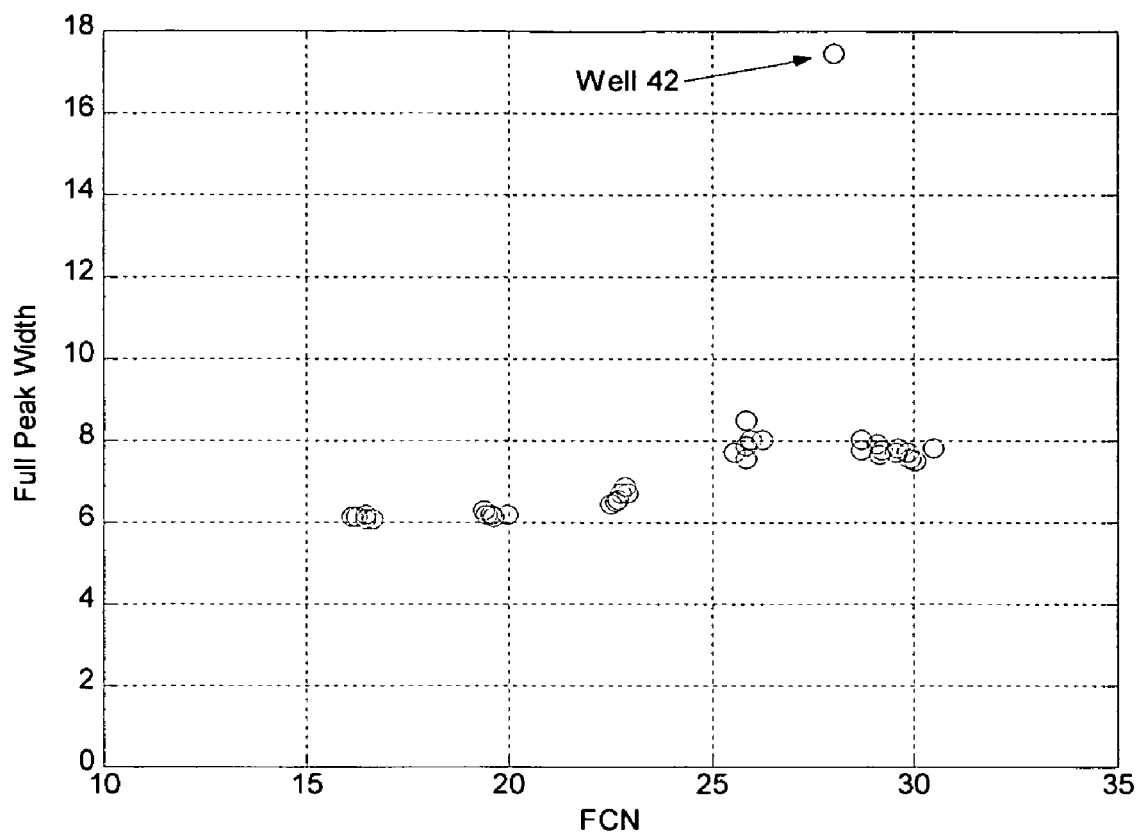
FIG. 29 illustrates experimental HIV results using the full peak width measurement to identify an abnormal response according to embodiments of this invention.

Peak width can be used to detect an abnormal assay response. The full peak width calculation was applied to the assay data that contained the abnormal response shown in FIG. 12. The results are presented in FIG. 29. As can be seen, normal responses for this data set produce full peak widths between about 6 and 9 cycles whereas full peak width of well 42 is 17.42. Accordingly, the amplification reaction of well 42 is abnormal and is disregarded.

The full peak width calculation will be affected by abnormal variations in amplification response that occur both before and after the reaction point value (e.g., the FCN) of the efficiency related value. Abnormal variations that occur after the reaction point value of the efficiency related value are not considered for an assay validity test, because they cannot affect assay quantification by the MR method. This option can readily be achieved using the half peak width calculation illustrated in FIG. 27 or its equivalent. In the illustrated example, only the width in periodic time units from about the half-maximum efficiency related transform up to about the reaction point value of the maximum efficiency related value is used. Of course, other suitable methods for measuring peak widths and half-peak widths are known in the art.

EXAMPLE 23

Software Embodiments

The systems of this invention can be incorporated into a multiplicity of suitable computer products or information instruments. Some details of a MR software implementation are provided below. Specific user interface descriptions and illustrations are taken to illustrate specific embodiments only and any number of different user interface methods known in the information processing art can be used in systems embodying this invention. The invention can also be used in systems where virtually all of the options described below are preset, calculated, or provided by an information system, and, consequently, provide little or no user interface options. In some cases, details and/or options of a prototype system are described for exemplification purposes; many of these options and/or details may not be relevant or available for a production system.

Furthermore, software embodiments can include various functionalities, such as, for example, processing reactions with one or two target reactions, or one or more internal control reactions, or reference data, or combinations of the foregoing. A software system suitable for use in this invention can provide any number of standard file handling functions such as open, close, printing, saving, etc.

Figure 30:
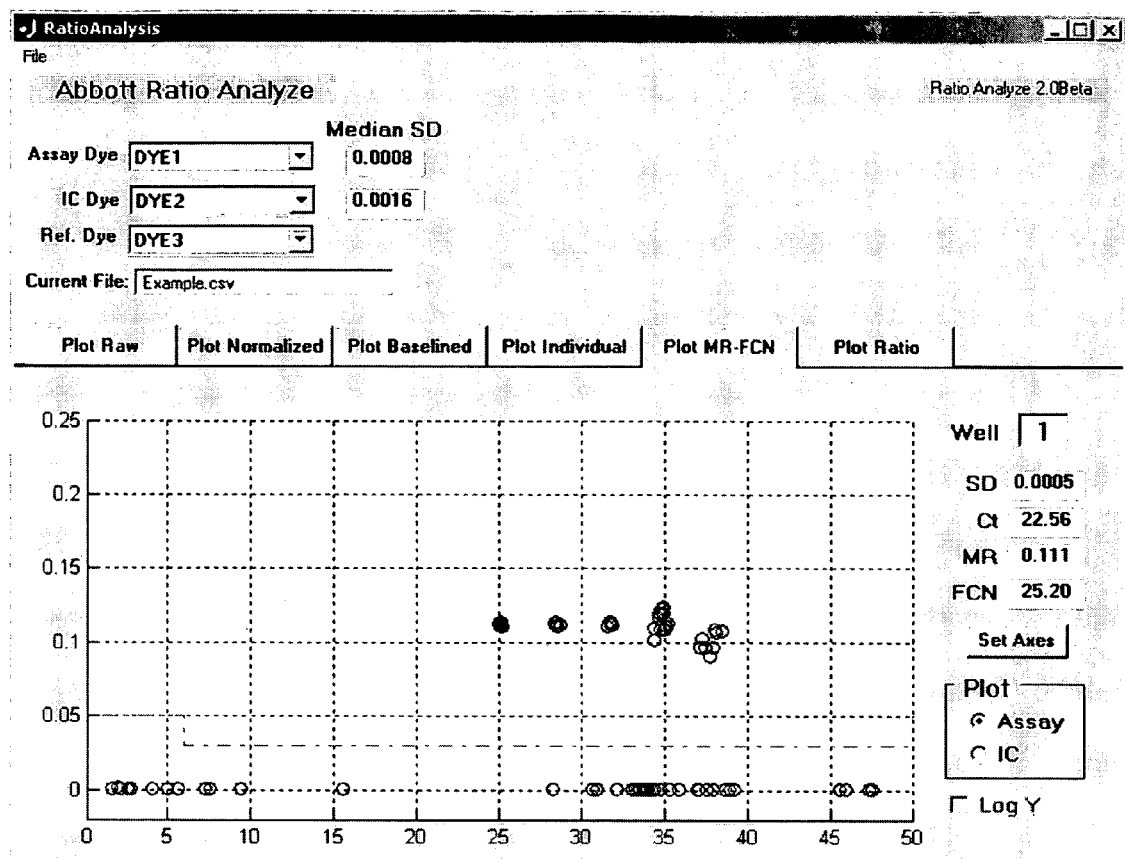
FIG. 30 illustrates an example of a user interface displaying an FCN-MR plot according to embodiments of this invention.
Figure 31:
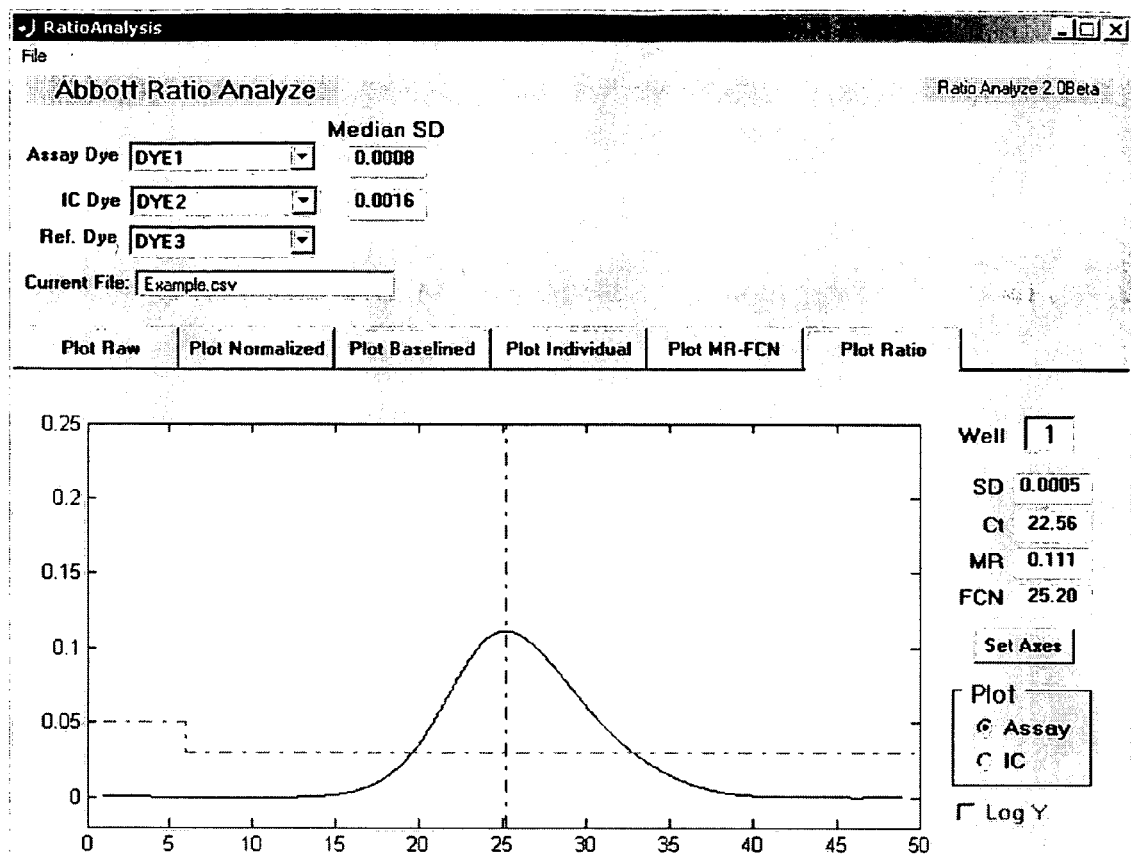
FIG. 31 illustrates an example of a user interface displaying a shifted ratio plot according to embodiments of this invention.

FIG. 30 illustrates a user interface for processing PCR data according to this invention. In this interface, the selection of appropriate dye(s) corresponding to the target assay, internal control, and reference responses are selected from popup lists in the upper left portion of the window. Tabs for selecting different viewing options are positioned in the middle of the window and are arranged horizontally. FIG. 30 shows that the tab displaying the MR-FCN plot has been selected. FIG. 31 illustrates a user interface showing the same data for well 1, but displaying the shifted ratio curve. Other tabs allow viewing of the raw fluorescence data, normalized fluorescence, and baselined data for all the responses. In addition, a tab allows inspection of each response individually. Fields to the right of the plot show calculated response values such as MR, FCN, $C_t$, and standard deviation in the baseline region. Below these calculated values are radio buttons allowing the user to display either the assay data or the internal control data.

Embodiment in a Programmed Information Appliance

Figure 32:
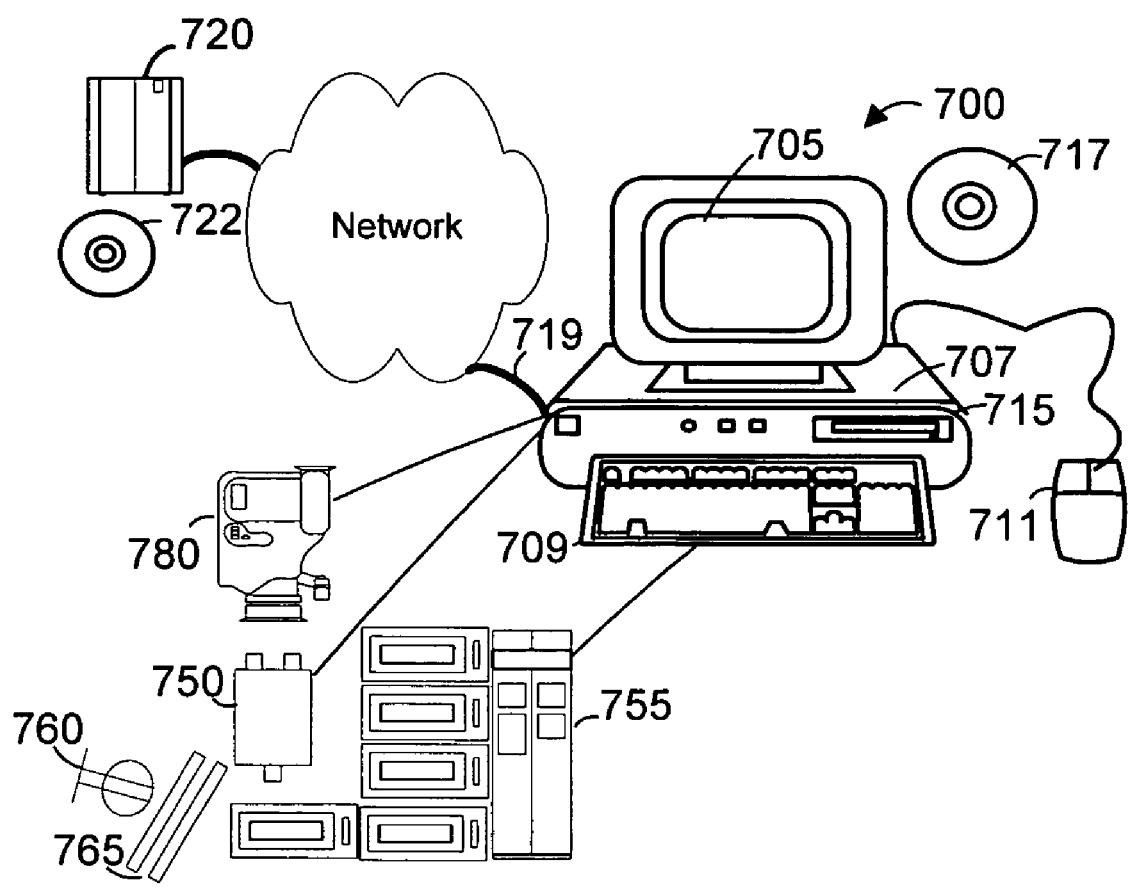
FIG. 32 is a block diagram showing a representative example of a logic device in which various aspects of the present invention may be embodied.

FIG. 32 is a block diagram showing an example of a logic device in which various aspects of the present invention may be embodied. As will be understood from the teachings provided herein, the invention can be implemented in hardware or software or both. In some embodiments, different aspects of the invention can be implemented in either client-side logic or server-side logic. Moreover, the invention or components thereof can be embodied in a fixed media program component containing logic instructions or data, or both, that when loaded into an appropriately configured computing device can cause that device to perform according to the invention. A fixed media component containing logic instructions can be delivered to a viewer on a fixed medium for physically loading into a viewer's computer or a fixed medium containing logic instructions can reside on a remote server that a viewer can access through a communication medium in order to download a program component.

FIG. 32 shows an information instrument or digital device 700 that can be used as a logical apparatus for performing logical operations regarding image display or analysis, or both, as described herein. Such a device can be embodied as a general-purpose computer system or workstation running logical instructions to perform according to various embodiments of the present invention. Such a device can also be customized and/or specialized laboratory or scientific hardware that integrates logic processing into a machine for performing various sample handling operations. In general, the logic processing components of a device according to the present invention are able to read instructions from media 717 or network port 719, or both. The central processing unit can optionally be connected to server 720 having fixed media 722. Apparatus 700 can thereafter use those instructions to direct actions or perform analysis as described herein. One type of logical apparatus that can embody the invention is a computer system as illustrated in 700, containing CPU 707, optional input devices 709 and 711, storage media 715, e.g., disk drives, and optional monitor 705. Fixed media 717, or fixed media 722 over port 719, can be used to program such a system and can represent disk-type optical or magnetic media, magnetic tape, solid state dynamic or static memory, etc. The invention can also be embodied in whole or in part as software recorded on this fixed media. Communication port 719 can also be used to initially receive instructions that are used to program such a system and represents any type of communication connection.

FIG. 32 shows additional components that can be part of a diagnostic system. These components include a viewer or detector 750 or microscope, sample handler 755, UV or other light source 760 and filters 765, and a CCD camera or capture device 780 for capturing signal data. These additional components can be components of a single system that includes logic analysis and/or control. These devices may also be essentially stand-alone devices that are in digital communication with an information instrument such as 700 via a network, bus, wireless communication, etc., as will be understood in the art. Components of such a system can have any convenient physical configuration and/or appearance and can be combined into a single integrated system. Thus, the individual components shown in FIG. 42 represent just one example system.

The invention can also be embodied in whole or in part within the circuitry of an application specific integrated circuit (ASIC) or a programmable logic device (PLD). In such a case, the invention can be embodied in a computer understandable descriptor language, which may be used to create an ASIC, or PLD, that operates as described herein.

Other Embodiments

The invention has now been described with reference to specific embodiments. Other embodiments will be apparent to those of skill in the art. In particular, a viewer digital information appliance has generally been illustrated as a computer workstation such as a personal computer. However, the digital computing device is meant to be any information appliance suitable for performing the logic methods of the invention, and could include such devices as a digitally enabled laboratory systems or equipment, digitally enabled television, cell phone, personal digital assistant, etc. Modification within the spirit of the invention will be apparent to those skilled in the art. In addition, various different actions can be used to effect interactions with a system according to specific embodiments of the present invention. For example, a voice command may be spoken by an operator, a key may be depressed by an operator, a button on a client-side scientific device may be depressed by an operator, or selection using any pointing device may be effected by the user.

It is understood that the examples and embodiments described herein are for illustrative purposes and that various modifications or changes in light thereof will be suggested by the teachings herein to persons skilled in the art and are to be included within the spirit and purview of this application and scope of the claims.

All publications, patents, and patent applications cited herein or filed with this application, including any references filed as part of an Information Disclosure Statement, are incorporated by reference in their entirety.

What is claimed is:

1. A method of determining whether a test sample contains a target nucleic acid, the method comprising:
    (a) contacting the test sample with at least one amplification agent for an amplification reaction;
    (b) measuring signals obtained at various points in the amplification reaction, the signals being proportional to the amount of the target nucleic acid present;
    (c) determining an efficiency related transform of the amplification reaction;
    (d) determining an efficiency related value that is the maximum magnitude of the efficiency related transform; and
    (e) determining that the test sample contains a target nucleic acid if the efficiency related value for the amplification reaction exceeds a criterion value wherein, the criterion value is determined by (1) amplifying a plurality of samples to determine the efficiency related values and (2) selecting a value that separates the efficiency related values of negative samples from the efficiency related values of positive samples.

2. The method of claim 1, wherein the efficiency related transform of the amplification reaction is selected from the group consisting of (1) ratio transform of the signals obtained from the amplification, (2) the derivative of the log of the signals obtained from the amplification, and (3) the first derivative of the signals obtained from the amplification.

3. The method of claim 2, wherein the efficiency related transform is the first derivative of the signals obtained from the amplification, wherein the first derivative of the signals obtained from the amplification reaction is equal to the difference between two consecutive signals obtained from the amplification reaction divided by the magnitude of the interval between the consecutive signals.

4. The method of claim 2, wherein the efficiency related transform is the first derivative of the signals obtained from the amplification, wherein the first derivative of the signals obtained from the amplification reaction is calculated by mathematical manipulation of a curve fitted to the signals obtained from the amplification reaction.

5. The method of claim 1, wherein the step of determining whether the efficiency related value exceeds a criterion value is performed by comparing the efficiency related value to a criterion curve, wherein the criterion curve is determined by:
    (a) performing a plurality of amplification reactions on negative samples, said negative samples being samples that lack the target nucleic acid;
    (b) determining the efficiency related value for each negative sample;
    (c) determining the mean and the standard deviation of the efficiency related values of the negative samples; and
    (d) determining that any sample having any efficiency related value exceeding the mean by a selected multiple of the standard deviation of the efficiency related values of the negative samples contains the target nucleic acid.

6. The method of claim 5, wherein any sample having any efficiency related value exceeding the mean by from one to about 20 times the standard deviation of the efficiency related transform of the negative samples is deemed to contain a target nucleic acid.

7. The method of claim 1, wherein the efficiency related value occurs at a particular reaction point and the selected value of step (e) varies according to the particular reaction point at which the efficiency related value occurs.

8. The method of claim 1, wherein the criterion value of step (e) is determined by (1) amplifying a plurality of samples to determine the efficiency related values and (2) selecting a value that is higher than all of the efficiency related values for negative samples.

9. The method of claim 1, wherein the efficiency related value is the maximum gradient of the log of the amplification response.

10. The method of claim 1, wherein the efficiency related value is the maximum ratio of the amplification response.

11. The method of claim 1, wherein the efficiency related value is the maximum first derivative of the amplification response.

12. The method of claim 1, wherein the efficiency related value is the maximum shifted ratio transform of the amplification response.

* * * * *